United States Patent
Becker et al.

(10) Patent No.: US 12,340,255 B2
(45) Date of Patent: Jun. 24, 2025

(54) EDGE DEVICE SERVICE ENCLAVES

(71) Applicant: Oracle International Corporation, Redwood Shores, CA (US)

(72) Inventors: David Dale Becker, Seattle, WA (US); Maxim Baturin, Sammamish, WA (US)

(73) Assignee: Oracle International Corporation, Redwood Shores, CA (US)

( * ) Notice: Subject to any disclaimer, the term of this patent is extended or adjusted under 35 U.S.C. 154(b) by 328 days.

(21) Appl. No.: 17/581,802

(22) Filed: Jan. 21, 2022

(65) Prior Publication Data

US 2022/0329578 A1  Oct. 13, 2022

Related U.S. Application Data

(60) Provisional application No. 63/173,244, filed on Apr. 9, 2021.

(51) Int. Cl.
*G06F 9/50* (2006.01)
*G06F 9/455* (2018.01)
(Continued)

(52) U.S. Cl.
CPC ............ *G06F 9/5077* (2013.01); *G06F 9/455* (2013.01); *G06F 9/5005* (2013.01);
(Continued)

(58) Field of Classification Search
CPC ............ H04L 41/0806; H04L 41/5041; H04L 41/5048; H04L 41/5051; H04L 9/08;
(Continued)

(56) References Cited

U.S. PATENT DOCUMENTS 10,880,743 B1   12/2020  Berzin et al.
11,050,781 B2 *  6/2021  Samuel ................ H04L 63/20
(Continued)

FOREIGN PATENT DOCUMENTS

CN     112543429 B    4/2022
EP     2369782        9/2011
(Continued)

OTHER PUBLICATIONS

AWS Snowball Edge Developer Guide AWS Snowball Edge, Available Online at: https://docs.aws.amazon.com/snowball/latest/developer-guide/AWSSnowball-dg.pdf#UsingCluster, 2021, 227 pages.
(Continued)

*Primary Examiner* — James N Fiorillo
(74) *Attorney, Agent, or Firm* — Kilpatrick Townsend & Stockton LLP

(57) ABSTRACT

Techniques are described for implementing a secure enclave within an edge device (e.g., an edge device of a computing cluster of edge devices). In some embodiments, a service enclave comprising a plurality of services can be implemented. The plurality of services can be implemented within respective containers and communicatively connected to one another via a virtual substrate network of the cloud-computing edge device. The virtual substrate network may be dedicated to network traffic between services of the plurality of services. A first service of the enclave may generate and transmit a message to a second service of the enclave for processing. One or more operations may be executed by the second service based on reception of the message.

20 Claims, 11 Drawing Sheets

(51) Int. Cl.
*G06F 11/34* (2006.01)
*H04L 41/50* (2022.01)

(52) U.S. Cl.
CPC ...... *G06F 11/3409* (2013.01); *G06F 11/3414* (2013.01); *G06F 11/3433* (2013.01); *G06F 11/3457* (2013.01); *G06F 2009/45562* (2013.01); *G06F 2009/45587* (2013.01); *H04L 41/50* (2013.01)

(58) Field of Classification Search
CPC ......... H04L 9/40; H04L 9/0897; H04L 12/46; H04L 12/462; H04L 12/4633; H04L 12/4641; H04L 45/00; H04L 49/00; H04L 63/06; H04L 63/20; H04L 63/162; H04L 63/0227; H04L 63/0272; H04L 63/0471; H04L 63/0478; H04L 63/0485; H04L 63/0876; H04L 67/10; G06F 3/06; G06F 3/067; G06F 3/0604; G06F 3/0622; G06F 3/0655; G06F 3/0659; G06F 3/0679; G06F 8/60; G06F 8/61; G06F 8/658; G06F 9/46; G06F 9/50; G06F 9/455; G06F 9/505; G06F 9/4401; G06F 9/4406; G06F 9/5055; G06F 9/5077; G06F 9/45558; G06F 11/14; G06F 11/1451; G06F 11/1469; G06F 2009/45562; G06F 2009/45587; G06F 2009/45595; G06F 2201/84
USPC .......................................................... 726/26
See application file for complete search history.

(56) References Cited

U.S. PATENT DOCUMENTS

| | | | |
|---|---|---|---|
| 11,201,789 B1* | 12/2021 | Keane | H04L 41/0893 |
| 11,582,027 B1 | 2/2023 | Lawton | |
| 2004/0252717 A1 | 12/2004 | Solomon et al. | |
| 2016/0266922 A1* | 9/2016 | Brandwine | G06F 21/62 |
| 2017/0201455 A1 | 7/2017 | Amulothu et al. | |
| 2018/0004953 A1* | 1/2018 | Smith, II | H04L 9/3268 |
| 2018/0054490 A1* | 2/2018 | Wadhwa | G08G 1/0129 |
| 2019/0138294 A1 | 5/2019 | Smith et al. | |
| 2019/0253262 A1* | 8/2019 | Smith | G06F 21/572 |
| 2019/0327312 A1 | 10/2019 | Gupta et al. | |
| 2020/0097274 A1 | 3/2020 | Sarkar et al. | |
| 2020/0103888 A1 | 4/2020 | Sayyarrodsari et al. | |
| 2020/0153623 A1 | 5/2020 | Asanghanwa et al. | |
| 2020/0213227 A1 | 7/2020 | Pianigiani et al. | |
| 2020/0293477 A1* | 9/2020 | Lefebvre | G06F 13/385 |
| 2020/0296138 A1* | 9/2020 | Crabtree | H04L 63/1425 |
| 2020/0344847 A1 | 10/2020 | Nardini et al. | |
| 2020/0351380 A1 | 11/2020 | Fedorov et al. | |
| 2021/0014113 A1* | 1/2021 | Guim Bernat | H04L 41/0273 |
| 2021/0112034 A1 | 4/2021 | Sundararajan et al. | |
| 2021/0132976 A1* | 5/2021 | Chandrappa | G06F 11/3006 |
| 2021/0168203 A1* | 6/2021 | Parulkar | G06F 11/2094 |
| 2021/0256824 A1 | 8/2021 | Wyseur et al. | |
| 2021/0314423 A1* | 10/2021 | Rolando | H04L 63/164 |
| 2022/0019422 A1 | 1/2022 | Anderson | |
| 2022/0051762 A1 | 2/2022 | Sharma et al. | |
| 2022/0083245 A1* | 3/2022 | Kant | G06F 3/0632 |
| 2022/0100182 A1 | 3/2022 | Mehrotra et al. | |
| 2022/0329628 A1* | 10/2022 | Zayats | H04L 41/5051 |
| 2022/0334725 A1* | 10/2022 | Mertes | G06F 3/065 |
| 2022/0405157 A1 | 12/2022 | Bender | |
| 2022/0413974 A1* | 12/2022 | Wang | G06F 11/203 |
| 2023/0254943 A1* | 8/2023 | Nardini | H04W 4/00 370/328 |
| 2023/0283517 A1* | 9/2023 | Maheshwari | G06F 11/3433 711/154 |
| 2024/0171391 A1* | 5/2024 | Ananthanarayanan | H04W 12/10 |

FOREIGN PATENT DOCUMENTS

| | | |
|---|---|---|
| EP | 3391588 | 10/2018 |
| WO | 2016069638 | 5/2016 |
| WO | 2019236181 | 12/2019 |
| WO | 2020052322 | 3/2020 |

OTHER PUBLICATIONS

Cisco SD-WAN Design Guide, Available Online at: https://www.cisco.com/c/en/us/td/docs/solutions/CVD/SDWAN/cisco-sdwan-design-guide.html, Sep. 2020, 102 pages.
Device Update APT Manifest, Available Online at: https://docs.microsoft.com/en-us/azure/iot-hub-device-update/device-update-apt-manifest, Feb. 17, 2021, 2 pages.
Encrypting Traffic Between Nodes with IPsec, Available Online at: https://docs.openshift.com/container-platform/3.11/admin_guide/ipsec.html, Accessed from Internet on May 21, 2021, 8 pages.
NSX-T Data Center, Available Online at: https://docs.vmware.com/en/VMware-NSX-T-Data-Center/2.5/nsxt_25_install.pdf, Jul. 31, 2020, 276 pages.
Software Installation and Upgrade for vEdge Routers, Available Online at: https://www.cisco.com/c/en/us/td/docs/routers/sdwan/configuration/sdwan-xe-gs-book/hardware-and-software-installation.html, 2021, 2 pages.
Upgrade an Edge Cluster, Available Online at: https://partners-intl.aliyun.com/help/doc-detail/154532.htm, 2021, 4 pages.
Upgrade NSX Edge Cluster, Available Online at: https://docs.vmware.com/en/VMware-NSX-T-Data-Center/3.1/nsxt_31_upgrade.pdf, 2021, pp. 1-57.
Akesson et al., How to Build a Resilient Over-the-Air Update Solution, Available Online at: https://techcommunity.microsoft.com/t5/internet-of-things/how-to-build-a-resilient-over-the-air-update-solution/ba-p/2163991, Mar. 2, 2021, 4 pages.
Asif et al., Prototype Implementation of Edge Encryption in IoT Architecture, 10th International Conference on Computing, Communication and Networking Technologies, Jul. 6-8, 2019, 7 pages.
Pavlik, Managing Thousands of Edge Kubernetes Clusters with GitOps, Available Online at: https://www.volterra.io/resources/blog/managing-thousands-of-edge-kubernetes-clusters-with-gitops, Dec. 18, 2019, 8 pages.
U.S. Appl. No. 17/549,859, Non-Final Office Action mailed on Oct. 16, 2023, 16 pages.
U.S. Appl. No. 17/549,859, "Final Office Action", mailed Jul. 5, 2024, 12 pages.

* cited by examiner

EDGE DEVICE SERVICE ENCLAVES

CROSS-REFERENCE TO RELATED APPLICATIONS

This non-provisional application claims priority to U.S. Patent Application No. 63/173,244, filed on Apr. 9, 2021, entitled "Cloud Computing Edge Computing Device (Rover)," the disclosure of which is herein incorporated by reference in its entirety for all purposes.

BACKGROUND

In cloud computing, processing and storage is generally performed by one or more service providers implemented at a centralized location. Data can be received from customers at the centralized location, processed there, and then the processed (or other) data can be transmitted back to customers. However, having a centralized location for cloud infrastructure components may not be ideal in various scenarios. For example, when there are hundreds or thousands of Internet of Things (IoT) devices transmitting data to the central servers, and especially when those IoT devices are not geographically close to the cloud infrastructure computing devices, conventional centralized systems are not ideal. These IoT devices may be considered on the "edge," as in they are not close to the central servers.

Additionally, there may be other instances when the centralized location for cloud components is less than ideal. For example, if the data is collected (e.g., by IoT devices) in a disconnected region or a location with no Internet connectivity (e.g., remote locations). Current centralized cloud computing environments may not meet time sensitivity requirements when streaming data due to the inherent latency of their wide-area network connections. Remotely generated data may need to be processed more quickly (e.g., to detect anomalies) than conventional centralized cloud computing systems allow. Thus, there are challenges with managing a traditional cloud computing environment that relies on centralized components.

BRIEF SUMMARY

Embodiments of the present disclosure relate to providing secure communication between services of one or more edge devices (e.g., via one or more service enclaves). A cloud-computing edge device can provide cloud computing or other distributed computing services at an "edge" location. A distributed computing cluster can be composed of a plurality of cloud-computing edge devices (referred to as "edge devices," for brevity) that collectively provide cloud-computing infrastructure and related services of a traditional cloud-computing environment outside a traditional cloud-computing environment. Some embodiments provide a method, a computing cluster, and a computer-readable medium that implement a service enclave (e.g., a service enclave of an individual edge device, a distributed service enclave between a plurality of cloud-computing edge devices, etc.). The service enclave, in some embodiments, may be used to implement distributed control plane for managing and provisioning cloud infrastructure resources among a computing cluster of edge devices in a similar manner as a traditional cloud-computing control plane. In some embodiments, a distributed data plane can be likewise be implemented within a service enclave. A "service enclave" refers to an isolated, intra-device network environment in which intra-service network traffic between a set of services (e.g., a predefined set of services) operating at an edge device is allowed. A service enclave may be isolated from network traffic provided by other components of the edge device using a virtual substrate network (e.g., a private virtual network that is dedicated to the set of services). In some embodiments, the virtual substrate network may span across multiple edge devices to enable services of one edge device in a computing cluster of edge devices to communicate with services of another edge device of the computing cluster. The edge devices of the computing cluster may be communicatively coupled (e.g., via physical wire and/or wireless technology).

One embodiment is directed to a method performed by an edge device (e.g., an edge device of a computing cluster that includes a plurality of cloud-computing edge devices). The method may include implementing, by a cloud-computing edge device, a service enclave comprising a plurality of services. In some embodiments, the plurality of services may be implemented within respective containers and communicatively connected to one another via a virtual substrate network of the cloud-computing edge device. The virtual substrate network may be dedicated to network traffic between services of the plurality of services. The method may further include generating, by a first service of the service enclave, a message comprising data related to cloud-computing operations. The first service of the service enclave may transmit the message comprising the data related to the cloud-computing operations. An additional message may be received via the virtual substrate network by the first service from a second service of the plurality of services. The first service may execute one or more operations based at least in part on receiving the additional message via the virtual substrate network.

In some embodiments, a network topology of the service enclave is predefined. In some embodiments, the plurality of services of the service enclave are individually implemented as a container (e.g., a Docker container) and share a common subnet.

In some embodiments, the service enclave is a first service enclave of a plurality of service enclaves, respective service enclaves of the plurality of service enclaves being implemented by a respective cloud-computing edge device of a plurality of cloud-computing edge devices that implement a distributed control plane of a distributed computing cluster, the plurality of service enclaves being communicatively connected via an intra-node switch. In some embodiments, the network traffic between the plurality of services of the first service enclave is unencrypted while external network traffic between the plurality of service enclaves of the plurality of service enclaves is encrypted.

In some embodiments, the plurality of services comprises a gateway service that enables and/or configured to enable communication between a client device and the plurality of services. In some embodiments, the virtual substrate network is communicatively connected to a virtual network interface card (e.g., a network interface card implemented with software) configured as an interface to one or more virtual machines hosted by the cloud-computing edge device.

Another embodiment is directed to a computing cluster that includes an intra-node switch and a plurality of cloud-computing edge devices communicatively connected to the intra-node switch and configured with one or more processors and one or more memories storing computer-executable instructions that, when executed by the one or more processors, cause the computing cluster to perform the method described in the preceding paragraphs. In some embodiments, the method is implemented by a single edge device.

Still another embodiment is directed to a non-transitory computer-readable medium storing computer-executable instructions that, when executed by one or more processors of a computing cluster, cause the computing cluster to perform the methods disclosed herein.

DETAILED DESCRIPTION

Figure 1:
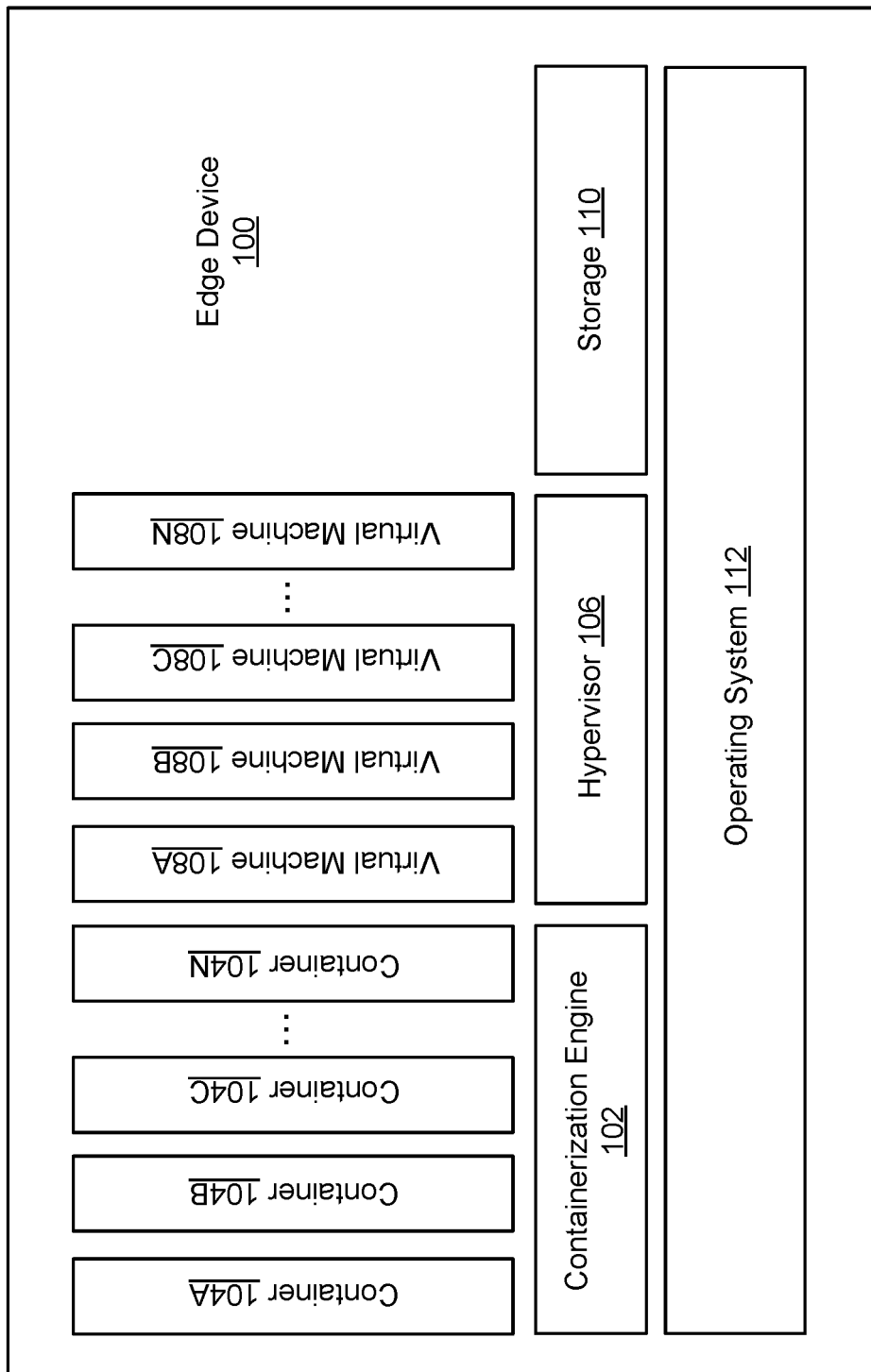
FIG. 1 is a block diagram of an example high-level architecture for a cloud infrastructure edge computing device, according to at least one embodiment.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Introduction

In some examples, a cloud-integrated edge service (e.g., implemented in an edge computing device) may be integral in addressing the desire to run time-sensitive cloud infrastructure application outside of a centralized data center (e.g., a datacenter of a cloud infrastructure service provider). Such an edge computing device may deliver computing and storage at the edge and/or in disconnected locations (e.g., remote locations separate from the centralized data center and lacking a public/private network connection (e.g., an Internet connection, a VPN connection, a dedicated connection, etc.) to enable low-latency processing at or near the point of data generation and ingestion. In some instances, a fleet of portable (which may be ruggedized for protection) server nodes (e.g., a fleet of edge devices) may be configured to physically bring the cloud infrastructure service to remote locations where cloud technology has been considered technologically infeasible or too cost prohibitive to implement.

To a customer (e.g., a user), the edge computing device can act as an extension of their cloud infrastructure: including virtual machines (VMs), containers, functions and data files, block volumes or object store services can also be delivered from the cloud infrastructure tenancy (e.g., a tenancy of the centralized cloud computing environment) with little to no modifications, and the customer experience may remain unchanged from that of the centralized cloud computing experience. Additionally, the edge computing device may be configured to implement both a control plane and a data plane that are part of a cloud infrastructure service provider. The data plane can be configured to manage data storage, migration, processing, etc., while the control plan can be configured for controlling the various services and architecture components of the computing device. Once the edge computing device is properly connected to a customer computing device (e.g., via a local area network (LAN)), the customer may be able to utilize the IaaS service (or at least a subset of it) using the same SDK and API used with the centralized cloud service.

The edge computing device can be delivered to a customer in a pre-configured form, such that the only action that might be required of the customer is to connect the nodes to a network (e.g., a local/on premise network that is accessible by a user computing device), power them up, and/or log in. The device can be pre-configured in various ways based on customer preference/request, or it can be in one of various configurations (e.g., storage-centric, compute-centric, etc.). The node or cluster of nodes can be portable and is intended to be mobile—when moved and set up again (or used while in motion), the deployment continues to run from where it turned off (or continuously). The edge computing device can also monitor for wide area network (WAN) connection availability (e.g., the Internet or the like), and can synchronize customer and management data with the cloud once connected to a WAN.

Some potential use cases for the edge computing device include: storage and processing, compute and input/output (I/O) intensive applications, machine learning, remote computing, low latency database and analytics, and data collection and migration. More specifically, the edge device can be used for storage and processing of large volumes of images, video, audio, and IoT sensor data generated in environments where WAN connection is latent or unavailable (e.g., in remote areas, an oil off-shore platform, or the like). Once this data is pre-processed, filtered, compressed, and/or secured it may be transported or transferred to the cloud service provider, where it can be further processed by the centralized server (e.g., traditional cloud service provider). The device can also be used for compute and I/O intensive applications, where low latency is paramount, such as tactical reconnaissance or 5G communications. The device can also be used for machine learning, with models trained in the cloud and running in disconnected locations to improve efficiency, intelligence, and/or productivity in manufacturing, document management, transportation, oil and gas mining, and/or telecommunications. It can also be used for remote computing requiring elevated security and airtight containment of data. Additionally, the device can be used for low latency database and analytics workloads, with more applications optimized over time. Further, the device can also be used for data collection and migration of large sets of object and database management system (DBMS) data into a cloud service provider, e.g., at faster speeds and lower cost than a WAN transfer.

The edge device can natively support distributed cloud paradigms, where complex, multi-stage compute workflows can be separated into individual components, which in turn can be deployed to the infrastructure of the edge device, on premise, and/or in the cloud. An example of such distributed workflow is represented in the following scenario. Massive amounts of data can be collected by an edge computing node deployed on an airplane (e.g., a military jet) in a reconnaissance operation with no Internet access (e.g., a disconnected edge computing device), where this data is be pre-processed in near real time by a machine learning model previously trained by the cloud service provider that provided the edge device. Even the first pass of processing the data with the models can detect significant anomalies and can alert personnel immediately—for example, a bridge may be destroyed and therefore the troops should be rerouted. When the airplane lands, the edge computing device can be physically connected to a network (e.g., an edge station potentially deployed at the airstrip). The pre-processed, filtered, smaller dataset can be loaded for final processing to a cluster of edge computing device nodes at the edge station. The original edge computing device can be released and can be loaded on another (or the same) airplane, for example to support the next mission. When processing at the edge station is complete, a 3D map update can be issued for immediate use. Change sets can then be uploaded by the edge station cluster to a datacenter and can be used to build future models providing intelligent tactical forecasts to the reconnaissance operation, or the like.

It should be appreciated that the following techniques may be employed in a variety of contexts such as telecommunications, oil and gas, healthcare, hospitality, agriculture, transportation, and logistics, and the like.

Embodiments described herein address these and other problems, individually and collectively. Specifically, embodiments of the present disclosure provide for a cloud infrastructure edge computing device.

Edge Device Architecture

An edge computing device (sometimes referred to as "a cloud edge device" or an "edge device," for brevity), extends a user's centralized cloud computing tenancy by physically putting customer infrastructure and platform services where data is generated—on the edge, on premise, or completely disconnected. Each deployment is created to address specific customer needs by provisioning VM instance images and data from the customer's centralized cloud tenancy. These workloads remain fully functional offline as the edge device adapts to the connection state, operates in harsh environmental conditions, and is ready to sync with the cloud whenever the connection is re-established.

FIG. 1 is a block diagram of an example high-level architecture for a cloud infrastructure edge computing device (e.g., edge device 100), according to at least one embodiment. An overview of the software and hardware component of the edge device 100 is provided below.

In some examples, the edge device 100 may include containerization engine 102 (e.g., Docker, Kubernetes, etc.) configured to implement one or more containers (e.g., corresponding to service(s) 104A, 104B, 104C, to 104N, collectively referred to as "service(s) 104"). A containerization engine (e.g., the containerization engine 102) may be container-orchestration system for automating computer application deployment, scaling, and management. In some embodiments, the containerization engine may be configured to provide OS-level virtualization to deliver software in packages called containers. These containers can be isolated from one another and utilize respective software, libraries, and configuration files, and can communicate with each other through well-defined channels. In some embodiments, service(s) 104 may include any suitable number of services (e.g., one or more). These services may implement at least some portion of centralized cloud capabilities. Each service may be stand-alone or operate as a distributed cluster. The edge device 100 may further include a hypervisor 106 configured to implement one or more virtual machines (e.g., virtual machines 108A, 108B, 108C, to 108N, collectively referred to as "virtual machine(s) 108" or "VMs 108").

In some examples, the edge device 100 includes storage 110 (e.g., object and/or block storage for storing local data). The edge device 100 includes operating system (OS) 112. In some embodiments, the OS 112 may be optimized for executing on an edge device and/or specific to execution on an edge device. OS 112 may be configured to manage the hardware of edge device 100 and supports a data plane of the services running on the edge device 100. The OS 112 may be configured to support a specific deployment type (e.g., a single edge device deployment, or a specific edge device cluster configuration). The OS 112 may be configured to secure the edge device by disallowing direct access by customers.

In some embodiments, the edge device 100 may include hardware such as any suitable number of central processing units (CPUs) and/or storage drives. For example, the edge device 100 depicted in FIG. 1 may have one, two, or more CPUs, with various numbers of cores per processing unit, and it may include any number of storage drives (e.g., 6.4 terabyte (TB) drives, or the like). As a non-limiting example, the edge device 100 may include block and/or object storage of any suitable size. The edge device 100 may include any suitable number of central processing units (CPUs), graphics processing units (GPUs), random access memory (RAM) of any suitable size, one or more ports (e.g., QSFP28, RJ45, dual ports, etc.), tamper-evident seals, or any suitable combination of the above components.

In some examples, the basic system functionality/services can be accessed via RESTful APIs have a custom load of software based on Linux. The virtual machine(s) 108 may individually be a Kernel-based Virtual Machines (KVM) and/or a hardware-based Virtual Machine (QEMU). Although storage 110 is represented as a separate component from the container(s) 104 and VM(s) 108, it can run as a container (e.g., container 104A) or in a VM (e.g., VM 108A). In some examples, it may be favorable to implement the storage 110 (e.g., object storage, block storage, etc.) as a container.

Figure 2:
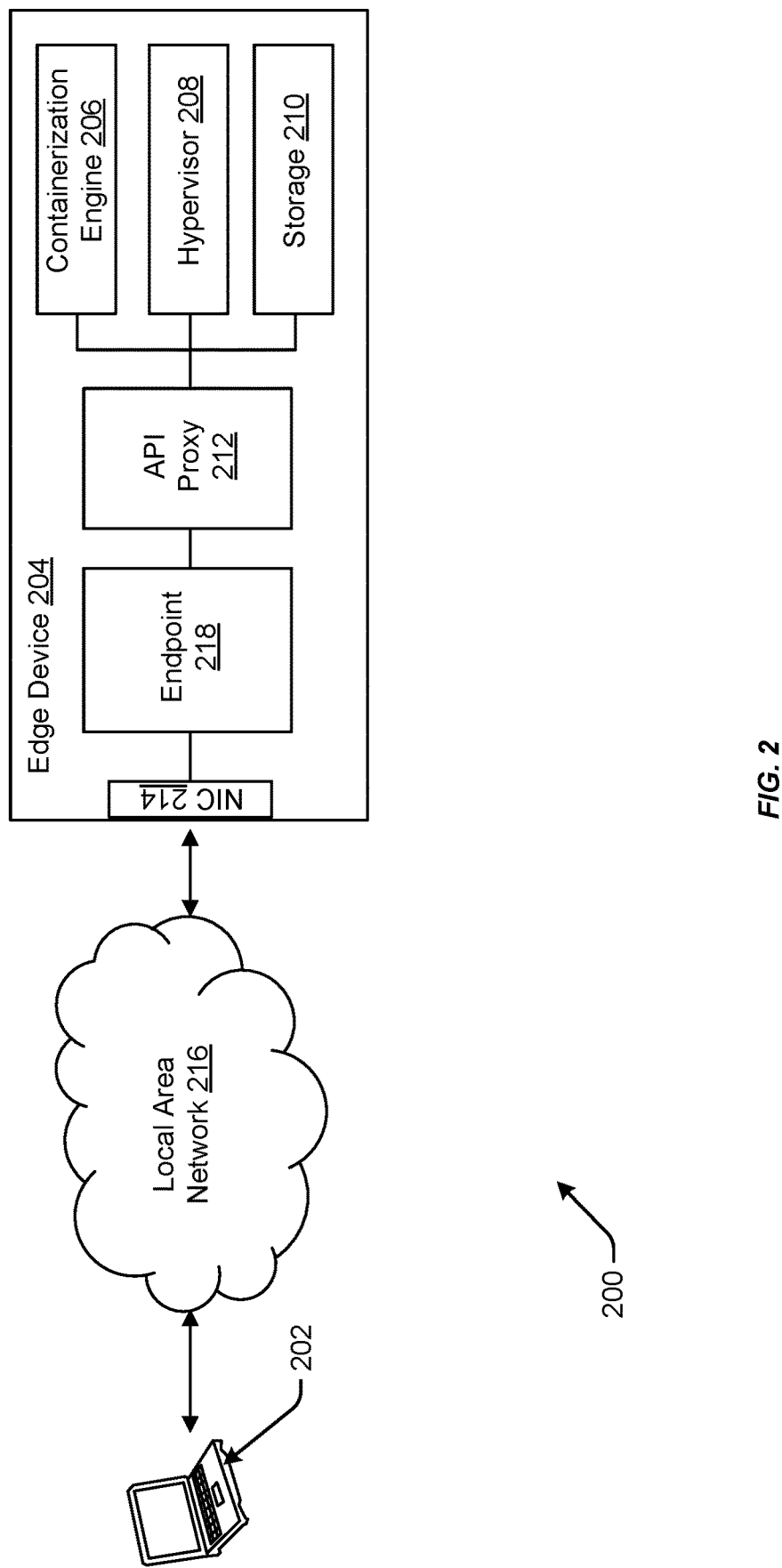
FIG. 2 is a block diagram of an example architecture for connecting a user computing device to a cloud infrastructure edge computing device, according to at least one embodiment.

FIG. 2 depicts an example architecture 200 for connecting the edge device described herein (e.g., edge device 100 from FIG. 1) to a computing device 202 (e.g., a user computing device). The computing device 202 can be any type of computing device including, but not limited to, a laptop computer, a desktop computer, or the like. The edge device 204 (an example of the edge device 100 of FIG. 1) may include containerization engine 206 (an example of the containerization engine 102 of FIG. 1), hypervisor 208 (an example of the hypervisor 106 of 1), and storage 210 (an example of the storage 110 of 1).

Additionally, as mentioned briefly above, the edge device 100 may include an API proxy 212 for managing the RESTful API calls received from the computing device 202. The API calls may enter the edge device 204 via a network interface card (NIC) 214 that is internal to the edge device 204. The network interface card 214 may be used to connect the edge device 204 to the computing device 202 via a local area network (e.g., the LAN 216). The API calls received by the NIC 214 may be transmitted to an exposed endpoint that may implement a Web server (e.g., endpoint 218). The web server can transmit the requests to the API Proxy 212, which can route the requests to the appropriate service (e.g., containerization engine 206, hypervisor 208, and/or storage 210). The exposed endpoint/web server may also be configured to implement the lightweight console that is for use by the customer (e.g., the user interface displayed on the computing device 202).

The lightweight console can run within a web browser (e.g., Mozilla Firefox, or the like) on a laptop computer, desktop computer, or other network-accessible device (e.g., connected to the local area network (LAN 216)) that is network-connected to the edge device 204 (e.g., via a router, cable, etc.). The edge device 204 can expose the endpoint 218 for the console connection, and the web server can transmit data to the web browser of the computing device 202 over the LAN 216.

Figure 3:
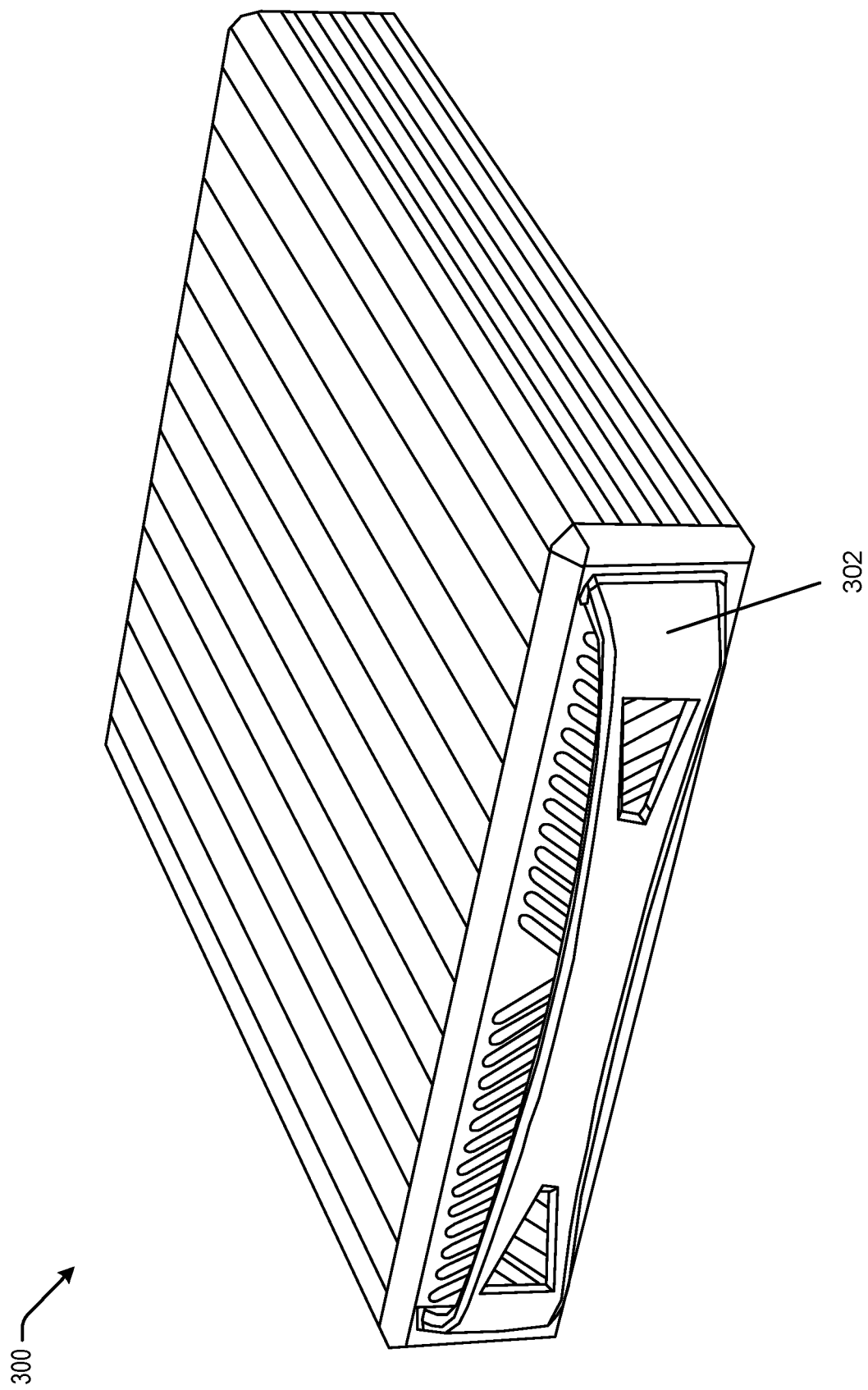
FIG. 3 is a block diagram of an example enclosure for a cloud infrastructure edge computing device, according to at least one embodiment.

FIG. 3 illustrates an example physical enclosure 300 of the edge device described herein (e.g., edge device 100 from FIG. 1). Various different form factors, shapes, colors, etc., can be employed to build a box (e.g., ruggedized) that can house the edge computing device. The physical enclosure can include handle 302, as shown, and may include tamper evident elements, so that if anyone breaks the enclosure open, it will be evident. In this way, the service provider that provides the edge computing device can ensure that the device is not modified. In some examples, the physical enclosure may not be possible to open. However, in some cases, it might be possible, but it would require extreme measures.

Figure 4:
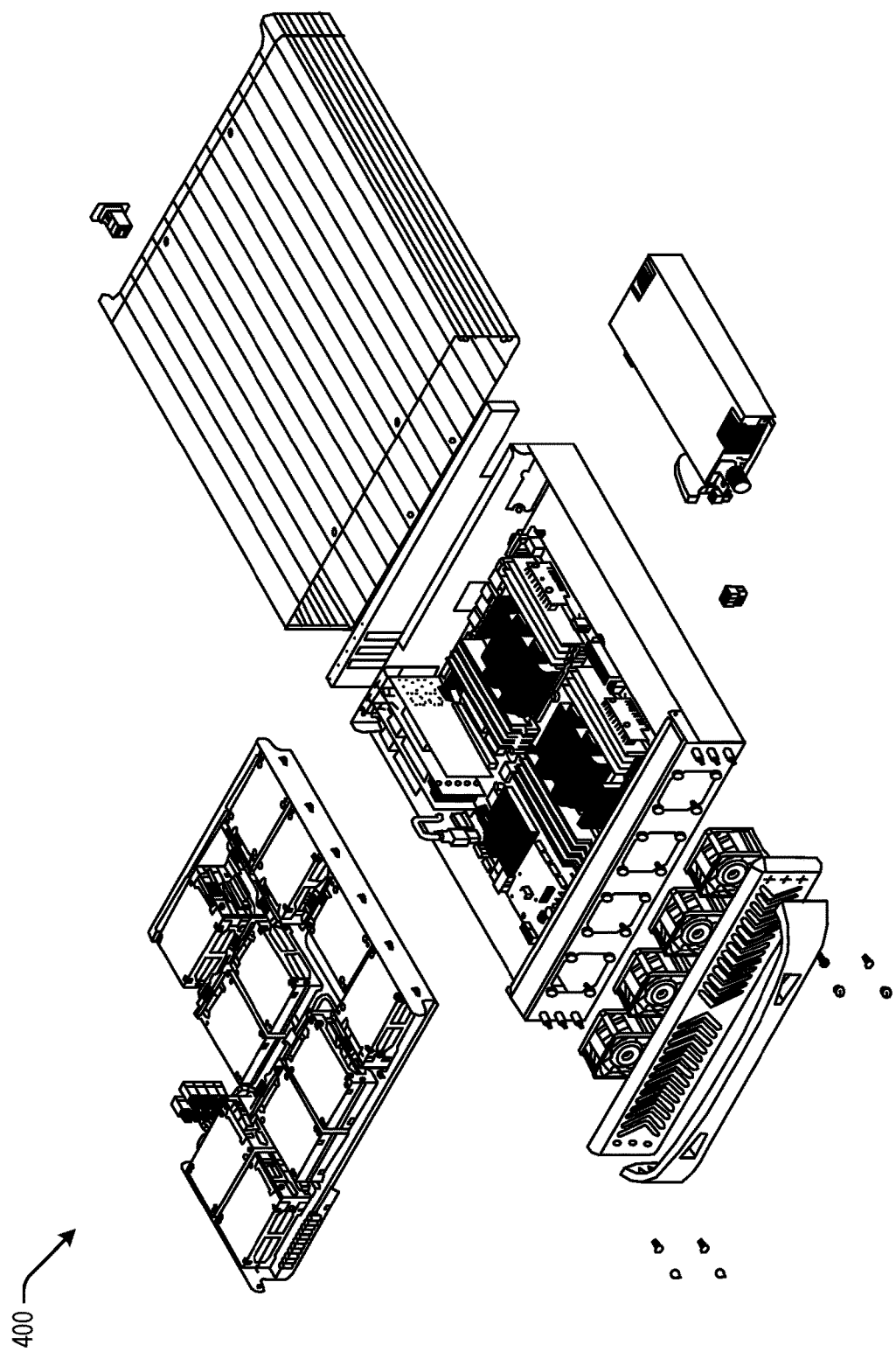
FIG. 4 illustrates an exploded view of the cloud infrastructure edge computing device described herein, in accordance with at least one embodiment.

FIG. 4 illustrates an exploded view of the cloud infrastructure edge computing device described herein (e.g., edge device 400, an example of the edge device 100 of FIG. 1), in accordance with at least one embodiment. The various components described with respect to FIGS. 1 and 2 can be communicatively attached to one or more motherboards and/or interface cards within the edge device 400. The illustrated configuration of components is but just one implementation. The specific locations of components shown is not intended to be limiting, and as noted, any configuration that is capable of implementing the functionality described herein is acceptable. Once the components are installed, the entire box can be closed, sealed, and locked with tamper-evident components.

The edge device 400 is a single enclosure. The enclosure may be designed to house any suitable number of serially attached SCSI (SAS) solid-state drives (SSDs) and all other components (e.g., CPU, memory, GPU, etc.) within the enclosure. The system may include one or more (e.g., 12 Gb) SAS connections to each drive in a fully contained sheet metal enclosure designed to fit within a standard 19" rack resting on an L bracket/shelf, on a table top or upright next to a desk with the use of a floor stand.

The system may include a tamper evident enclosure, front security plugs covering screws holding a front bezel in place with rear security interlock features. In some embodiments, the system may include a dual socket motherboard and any suitable amount of DRAM. In some embodiments, the system may include any suitable number (e.g., 2, 3, etc.) SATA SSDs, storage controllers, embedded network connections, one or more ports (e.g., dual ports, serial ports, etc.), one or more fans as part of a cooling system, or any suitable combination of the above.

As a non-limiting example, the edge device 400 may be made up of an external extruded aluminum case secured in the front with a vented bezel and rear panel only exposing I/O connections required for data transfer and management. Mounting can be designed to mount the any suitable motherboard, fans, and power supply.

Figure 5:
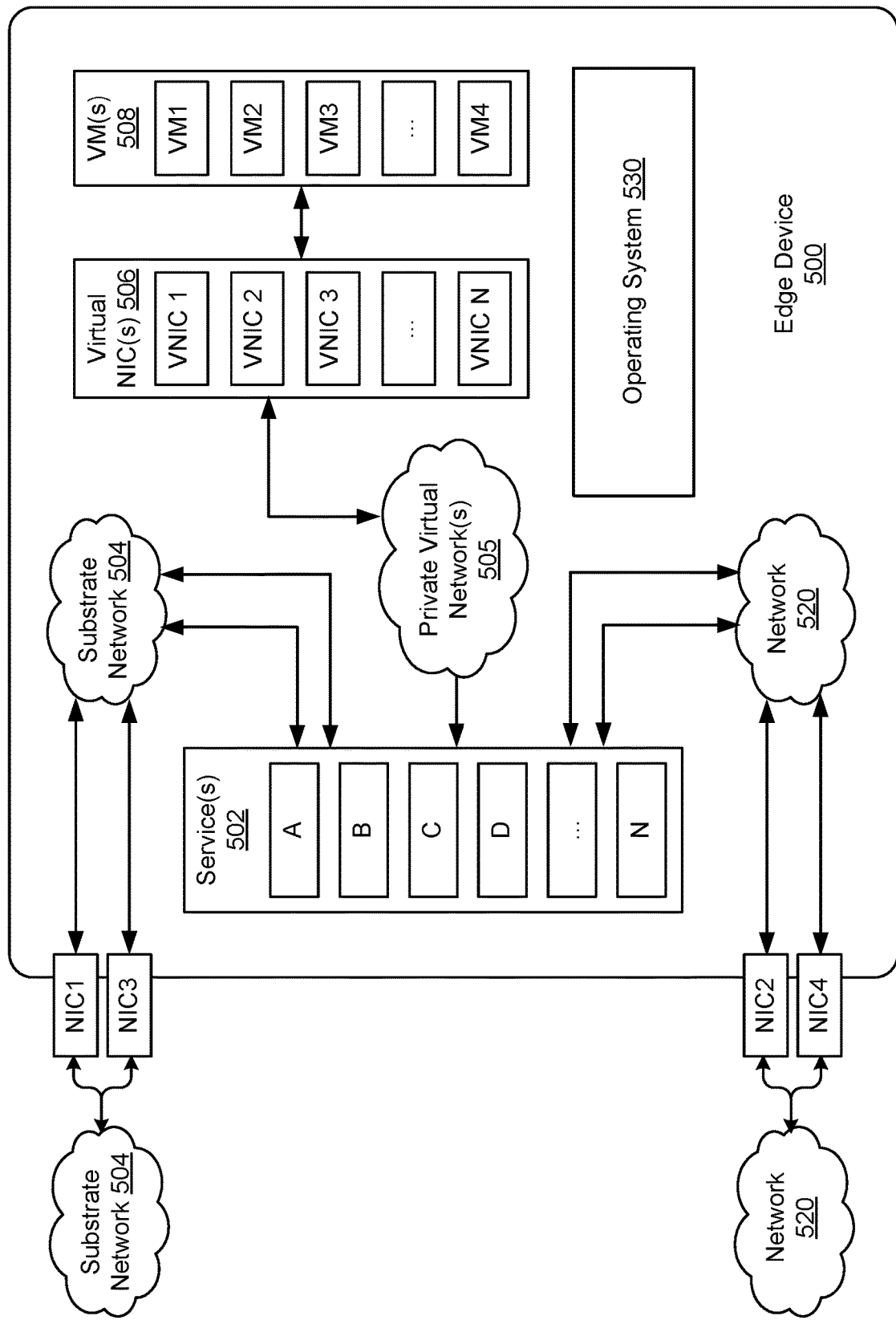
FIG. 5 is a block diagram of an example computer architecture of a cloud infrastructure edge computing device, according to at least one embodiment.

FIG. 5 is a block diagram of an example computer architecture 500 of a cloud infrastructure edge computing device (e.g., edge device 500, an example of the edge devices 100 and 204, of FIGS. 1 and 2, respectively), according to at least one embodiment. The edge device 500 can be thought of as a cloud-integrated service that extends some or all of conventional cloud capabilities to locations outside of cloud data centers. This can be achieved via portable ruggedized server nodes that provide cloud-like functionality in locations with no WAN connectivity. This allows customers to shift select cloud workloads to remote locations and enable intensive data processing operations close to the data ingestion points at the edge of their cloud infrastructure.

The edge device 500 may include any suitable number of services (e.g., service(s) 502). Each service may run as a container (e.g., a Docker container) locally on the edge device 500. The service(s) 502 may be communicatively connected via a substrate network 504 such that the communications between services are encrypted (e.g., in accordance with a security protocol such as MACsec). Each container may be assigned a substrate IP address (e.g., a static address) with which traffic can be addressed. In some embodiments, a security protocol (e.g., MACsec) is configured at provisioning time (e.g., before the edge device 500 is shipped to the user). The edge device's system software (including service(s) 502) may execute in the secure environments protected by boot security software (e.g., Trenchboot Secure Launch). Users may be restricted from accessing the secure environment and/or the substrate network 504. To minimize the amount of resources used by these services the service code may be compiled and saved to disk to decrease RAM space as well as decrease the CPU load on the edge device 500.

Some example services included in service(s) 502 may include a UI console service, an identity control plane (CP) service, an identity data plane (DP) service, a compute application programming interface (API) service, a compute worker thread service, a virtual network (VN) API service, a block storage API service, a function-as-a-service service, an events service, an object storage management service (e.g., implementing a storage platform such as Ceph Storage, a product of Red Hat, Inc.)), a compute DP service (e.g., an example of hypervisor 208 of FIG. 2), a VN DP service, a block storage management service, a function-as-a-service API service, a function-as-a-service load balancing (LB) service, a function-as-a-service process thread service, a distributed data store management service (e.g., etcd3), a dynamic host configuration protocol service, a domain name system service, a network time protocol (NTP) service, to name a few. Some example functionality provided by these services is discussed below.

By way of example, compute DP service may be configured (e.g., preconfigured and provisioned onto the edge device 500) to isolate the VM(s) 508 on the same hypervisor host. The compute DP service can utilize any suitable container engine (e.g., Docker container, MicroContainer, or the like) to isolate the VM(s) 508 on the same hypervisor host from each other. The compute DP service may utilize any suitable hypervisor (e.g., Quick EMUlator (QEMU), Kernel-based Virtual Machine (KVM), etc.) to provide virtual hardware emulation for VM(s) 508. In some embodiments, VNIC(s) 506 are attached to subnets of any suitable number of virtual networks (e.g., private virtual network(s) (PVN(s))) 505 and are assigned private Internet Protocol (IP) addresses. One VM may have multiple VNICs from different VCNs and different subnets. The maximum number of VNICs can be limited by predefined thresholds (e.g., configuration data referred to as "VM shape" that defines VNICs per VM count, VNIC shape, etc.). In some embodiments, the predefined thresholds are applied to each of the VM(s) 508. The subnets utilized by the VNIC(s) 506 may be isolated by VLANs. In some embodiments, some or all of the VNIC(s) 506 may be assigned public and/or private IP addresses. A public IP address is an address in the network(s) 520, while a private IP address refers to an IP address of the PVN(s) 505.

In some embodiments, the edge device 500 implements various networking functionality via a number of services such as a network address translation (NAT) service, a dynamic host configuration protocol (DHCP) service, a domain name system (DNS) service, a network time protocol (NTP) service, a metadata service, and a public API service). The metadata service may provide initialization data and other metadata to all VM(s) 508. In some embodiments, DHCP service assigns private IP addresses to each of the VNIC(s) 506, each of the VM(s) 508 having one or more VNICS. DNS service may provide domain name resolution to VM(s) 508 on the edge device 500. NTP may provide time synchronization to VM(s) 508. In some embodiments, a public IP service executing as part of service(s) 502 may enable a VM to access a public API without assigning the VM a public IP and without configuring a service gateway.

In some embodiments, at least one of the VM(s) 508 may implement block (or object) storage. In some embodiments, the hypervisor associated with a virtual machine may include a library that enables the hypervisor to use a distributed data storage platform (e.g., Ceph). The library may utilize a protocol associated with that storage platform (e.g., RADOS Block Device (RBD) to facilitate storage of block-based data. The distributed data storage platform may be implemented over multiple virtual machines. In some embodiments, the distributed data storage platform supports making snapshots and copying block volumes. VM images and VM block volumes can be Ceph block devices. In some embodiments, the VM(s) implementing the distributed data storage platform will use system reserved resources (e.g., 8 CPU cores, some of the total number of CPUs available on the edge device 500). For example in order to provision a boot volume, a block device image may be copied to a boot volume of the block device. The distributed data storage platform may use block devices include multiple nodes for redundancy. If some node fails then the block device can continue to operate. In some embodiments, the distributed data storage platform (e.g., Ceph), automatically recovers the block device data in case of a few node failures. Block storage may be utilized to store images for any suitable deployable resource. By way of example, an image may be utilized for launching VMs. In some embodiments, the image may correspond to a particular VM shape (e.g., a compute heavy VM, a GPU optimized VM, a storage VM, and the like).

Compute API service may support the following operations: 1) VM launch and terminate, 2) VM stop, start, reboot, 3) List VMs and/or get information on a specific VM, 4) obtain VM console history API, 5) obtain a VM snapshot, 6) attach/detach block volumes, and the like. In some embodiments, Compute API service can be used to call other services (e.g., compute DP service, identity DP service for authentication and authorization, etc.).

Some of the functionality of other services will be discussed in connection with FIG. 7. In general, although each service may not be discussed in detail herein, the general functionality provided by the service(s) 502 may include the functionality of cloud services provided by a remote cloud service provider. In some embodiments, the edge device 500 may be associated with a predefined region and/or realm such that some of the service(s) 502 may operate as if they were operating in a cloud computing environment, despite the fact they are operating on one or more local device(s) (one or more edge devices) as a single instance or as part of a distributed service that may have no or intermittent public network access to a cloud computing environment associated with the customer.

In some embodiments, the edge device 500 may provide any suitable number of virtual networks (e.g., private virtual network(s) 505) using compute, memory, and networking resources (e.g., virtual network interface card(s) (VNIC(s) 506)). A virtual network is a logical network that runs on top of a physical substrate network. Using the service(s) 502, one or more customer resources or workloads, such as virtual machines (e.g., virtual machine(s) (VM(s)) 508, executing a compute instance) can be deployed on these private virtual networks. Any suitable combination of VM(s) 508 can execute functionality (e.g., a compute instance, storage, etc.) which is individually accessible through a virtual NIC (e.g., one of the virtual NIC(s) 506). Each VM that is part of a PVN is associated with a VNIC that enables the VM (e.g., a compute instance) to become a member of a subnet of the PVN. The VNIC associated with a VM facilitates the communication of packets or frames to and from the VM. A VNIC can be associated with a VM when the VM is created. PVN(s) 505 can take on many forms, including peer-to-peer networks, IP networks, and others. In some embodiments, substrate network traffic of the service(s) 502 may be encrypted and/or isolated (e.g., by virtue of different PVNs or subnets) from network traffic of one or more the VM(s) 508 executing on the edge device 500.

The edge device 500 thus provides infrastructure and a set of complementary services that enable customers to build and run a wide range of applications (e.g., compute instances), services, and/or storage in a highly available, physically local, and virtual hosted environment. The customer does not manage or control the underlying physical resources provided by the edge device 500 but has control over expanding or reducing virtual machines (e.g., compute instances, virtual NICs, block or object storage, etc.), deploying applications to those virtual machines, and the like. All workloads on the edge device 500 may be split into different CPU sets (e.g., VM and non-VM). One set (e.g., non-VM such as workloads performed by the service(s) 502) may utilize a subset of CPU cores (e.g., 8) of the edge device 500, while the other set (e.g., VM workloads performed by the VM(s) 508) may utilize a different subset of CPU cores.

The edge device 500 may be communicatively connected to a user device (e.g., the computing device 202 of FIG. 2) via one or more network interfaces (e.g., NIC2 and/or NIC 4) and network 520 to interact and/or manage the VM(s) 508. In certain embodiments, a lightweight console can be provided at the user device via a web-based user interface that can be used to access and manage the edge device 500. In some implementations, the console is a web-based application (e.g., one of the service(s) 502) provided by the edge device 500.

FIG. 5 depicts a single edge device. However, it should be appreciated that more than one edge device may be utilized as a distributed computing cluster.

Figure 6:
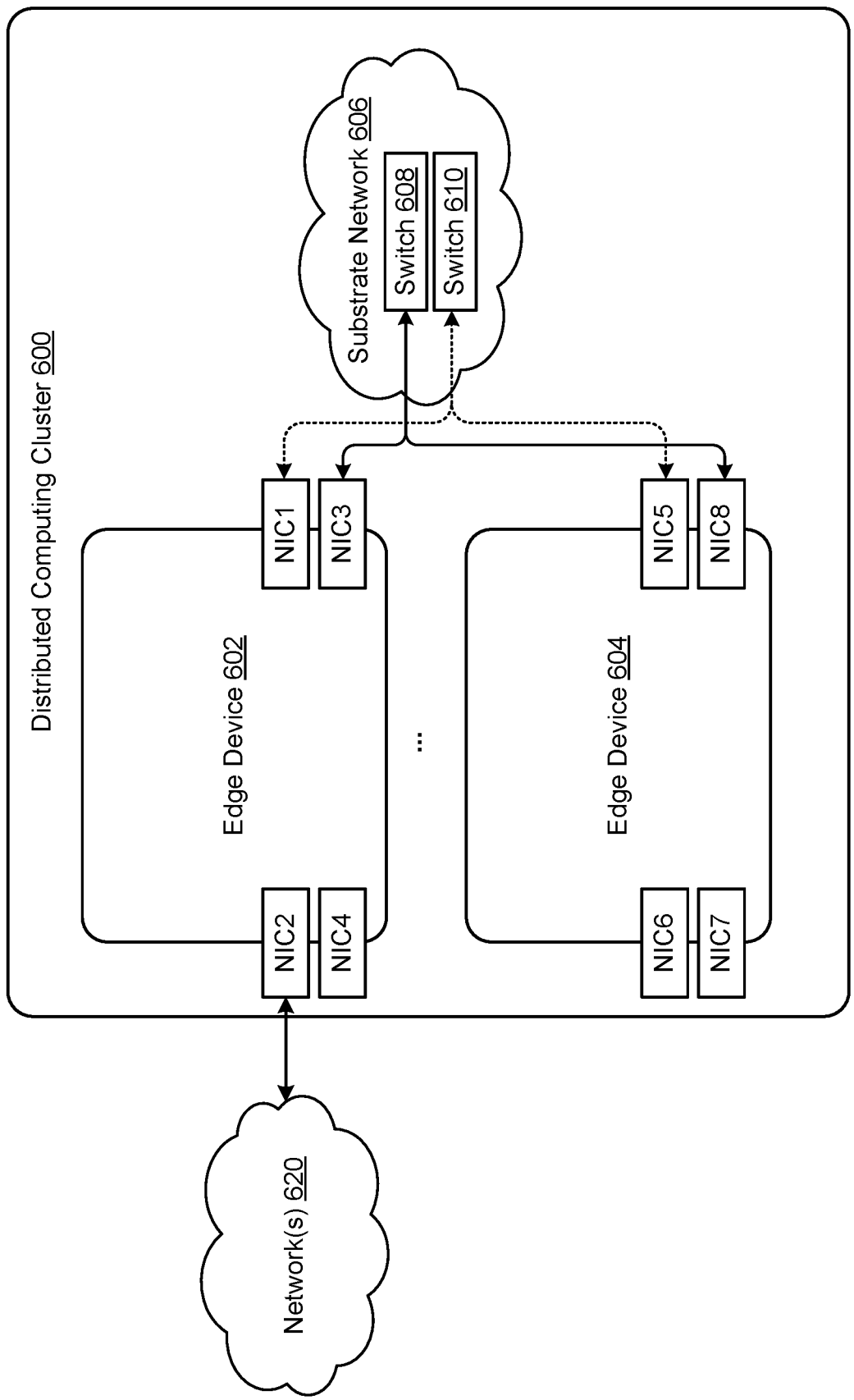
FIG. 6 is a block diagram depicting a distributed computing cluster that includes one or more edge computing devices, according to at least one embodiment.

FIG. 6 is a block diagram depicting a distributed computing cluster 400 that includes one or more edge computing devices (e.g., edge device 602 and 604, each an example of the edge device 500 of FIG. 5), according to at least one embodiment.

Each edge device of the distributed computing cluster 600 may be connected via substrate network 606 (an example of the substrate network 504 of FIG. 5. In some embodiments, the edge devices of the distributed computing cluster 600 (sometimes referred to as "edge computing nodes" or "edge nodes") may be connected by the substrate network 606 using one or more switches (e.g., switch 608 and/or 610). In some embodiments, NIC1 and NIC5 may include a particular connector (e.g., RJ45 connector) while NIC3 and NIC8 may include the same or a different connector (e.g., a QSFP28 100 GbE connector). In some embodiments, only one edge device of the distributed computing cluster 600 is connected to a customer network such as network(s) 620 (an example of the network(s) 520 of FIG. 5). Thus, not only may traffic between services of an edge device be encrypted and isolated from other traffic of a given edge device, but traffic between distributed services operating across multiple edge devices may also be encrypted and isolated from other traffic of the computing cluster. In some embodiments, each edge device is preconfigured as a particular node in the distributed computing cluster 400. In other embodiments, the user can configured the number and topology of the edge devices of the distributed computing cluster 600.

Figure 7:
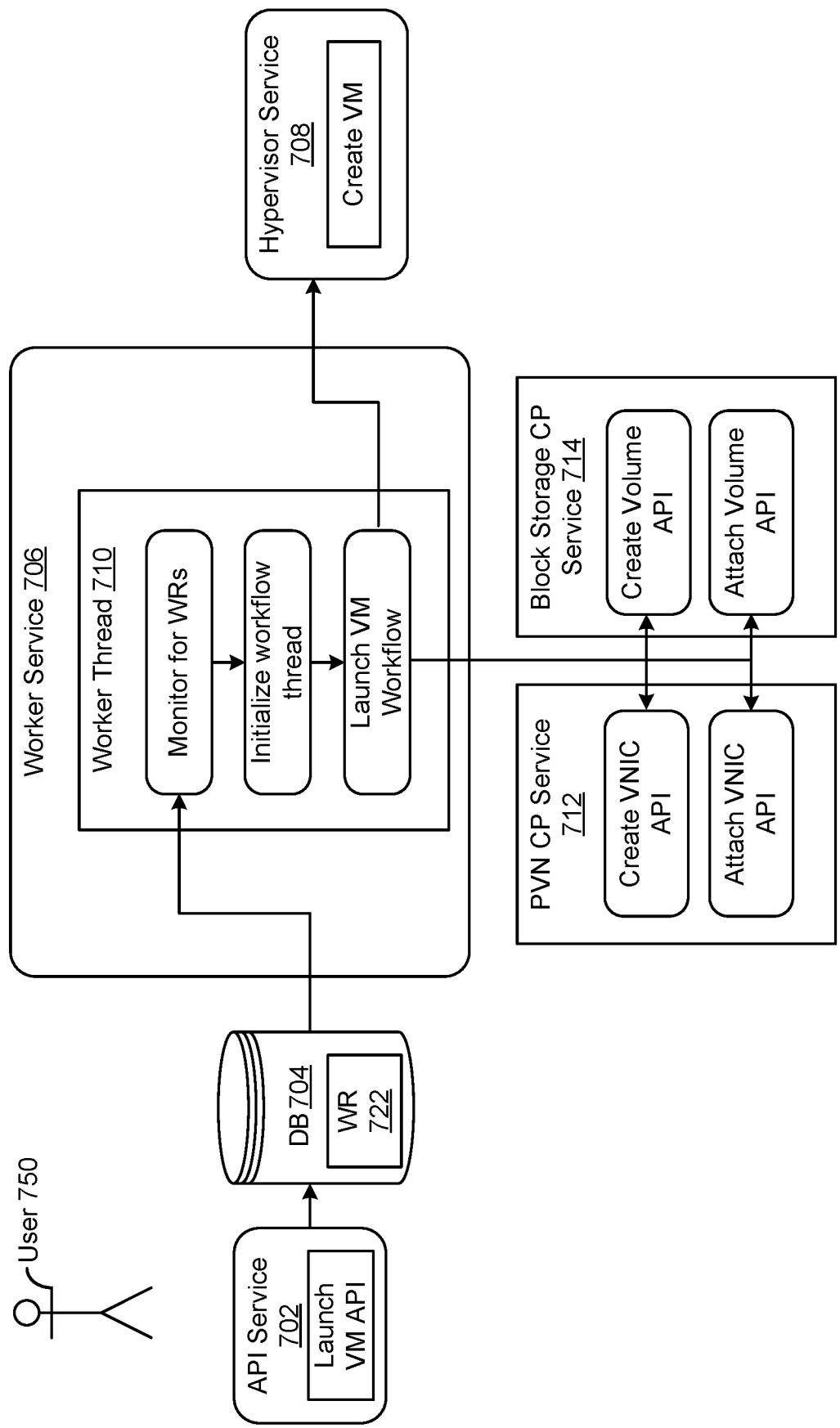
FIG. 7 is a block diagram depicting a control plane and flow for executing a workflow by one or more components of a cloud infrastructure edge computing device, according to at least one embodiment.

FIG. 7 is a block diagram depicting a flow 700 for executing a workflow by one or more components of a cloud infrastructure edge computing device, according to at least one embodiment. Components that execute the flow 700 may include API service 702, database 704, service 706, hypervisor service 708, PVN CP service, Block storage CP service 714, although more or fewer services may be included. In some embodiments, each of the services of FIG. 7 are an example of a service of the service(s) 502 of FIG. 5. In some embodiments, at least some of the functionality discussed in connection with the services of FIG. 7 may be combined in any suitable combination and provided as a single service or instances of the same service. By way of example, in some embodiments, the functionality of services 702-708 may be provided by a single service (e.g., compute CP service discussed above in connection with FIG. 5). In some embodiments, the functionality provided by the services 702-708 may be provided by a single edge device (e.g., edge device 500 of FIG. 5) or by two or more edge devices (e.g., by edge device 602 and edge device 604 of FIG. 6).

In some embodiments, the API service 702 may be configured to accept work requests that include intended state data that describes an intended state of a set of data plane resources (e.g., VM(s) 508 of FIG. 5). As a non-limiting example, user 720 may utilize a user device (e.g., the user device 202 of FIG. 2) to access a user interface with which he can make various selections indicating a desire to launch a VM. The user input may be received by the API service 702 (an example of the compute CP service of FIG. 5) which may generate a work request (e.g., WR 722) and utilize a predefined Launch VM API to store the work request in a distributed database (e.g., DB 704). In some embodiments, the DB 704 may be a computing cluster which is configured to use etcd3 as an immediately consistent, highly-available, transactional, distributed database. Generally, a work request indicates a desire and information needed to create and/or modify data plane resources such as VM(s) 508. In some embodiments, the work request includes state information indicating a desired state for the data plane resource. In some embodiments, the DB 704 may be accessible to all services operating on any edge device (and by services operating on any suitable edge device of an edge device cluster such as distributed computing cluster 600).

Service 706 (e.g., also an example of the compute CP service of FIG. 5) may be configured to execute one or more worker processes (e.g., computing thread 710). Some of these worker processes may be configured by the service 706 at any suitable time to execute a continuous and/or ongoing predefined workflow. By way of example, the service 706 may configure one or more worker threads (e.g., including computing thread 710) to monitor the DB 704 for new work requests (e.g., WR 722). The computing thread 710 may be configured to determine if a work request WR 722 is already being attended to. In some embodiments, this entails checking a predefined storage bucket within DB 704 for a unique identifier associated with WR 722. If the unique ID included within WR 722 does not appear in the bucket (or the WR is otherwise indicated as having not been picked up for processing), the computing thread 710 (e.g., a nanny thread) may initialize a workflow thread (e.g., another instance of a computing thread 710) which may then be configured by the computing thread 710 to execute a workflow corresponding to launching a VM corresponding to the WR 722.

The initialized workflow thread may be communicatively coupled (e.g., via the substrate network 504 of FIG. 5) to a workflow service (not depicted). The workflow service may be configured to identify, from one or more predefined workflows, one that corresponds to launching a VM, and therefore, to the work request 722. These predefined workflows identify one or more steps/operations to be taken, and a sequence to those steps, in order to achieve a predefined goal (e.g., launching a virtual machine, stopping/starting a virtual machine, terminating a virtual machine, creating a block volume, removing a block volume, etc.). The workflow thread may launch the VM workflow and oversee its execution by various other entities. In some embodiments, the workflow thread may pass any suitable portion of the intended state data of the DP resource to any suitable combination of services.

As a non-limiting example, as part of the workflow for launching a virtual machine (e.g., a VM to be hosted by hypervisor service 708), one or more APIs can be called for creating and attaching the VNIC. Similarly, a number of APIs may be provided for creating and/or attaching a block storage volume API. In some embodiments, the workflow thread may perform any suitable call to one or more APIs to invoke the functionality of PVN CP Service 712, which in turn may be configured to create and attach a VNIC. The workflow thread may then call block storage CP service 714 which may then execute any suitable operations to create and attach a block storage volume. The worker thread overseeing the workflow may ensure a designated order (e.g., create the VNIC first before creating the block volume). This worker thread may be configured to catch any errors and/or exceptions from one or more services it has invoked. If no exceptions/errors are encountered, the worker thread overseeing the workflow can provide any suitable data to the hypervisor service 708 (via the substrate network), which in turn, execute functionality for creating the VM requested. The hypervisor service 708 may provide actual state data for the newly launched VM. In some embodiments, the worker thread overseeing the workflow can store the actual state data in the DB 704 for later reference (e.g., when a monitor may determine whether the actual state data matches the requested state data indicating no changes needed or when the actual state data fails to match the requested state data, indicating a change of the data plane resources is needed).

In some embodiments, the workflow thread may be communicatively coupled to a cluster manager (not depicted). Cluster manager may be configured to manage any suitable number of computing clusters. In some embodiments, the cluster manager may be configured to manage any suitable type of computing cluster (e.g., a Kubernetes cluster, a set of computing nodes used to execute containerized applications, etc.). The workflow thread may be configured to execute any suitable operations to cause the cluster manager to execute any suitable orchestration operation on the DP resource(s) (e.g., a VM) in accordance with the instructions identified to bring the DP resource(s) in line with the intended state data. In some embodiments, a monitoring entity (e.g., the workflow thread, a thread launched by the workflow thread) may be communicatively coupled to DP resource(s) 116 and configured to monitor the health of DP resource(s). In some embodiments, the monitoring entity may be configured to store any suitable health data in the DB 704.

The specific operations and services discussed in connection with FIG. 7 is illustrative in nature and is not intended to limit the scope of this disclosure. The particular operations performed and services utilized may vary depending on the particular workflow associated with the requested operations.

Figure 8:
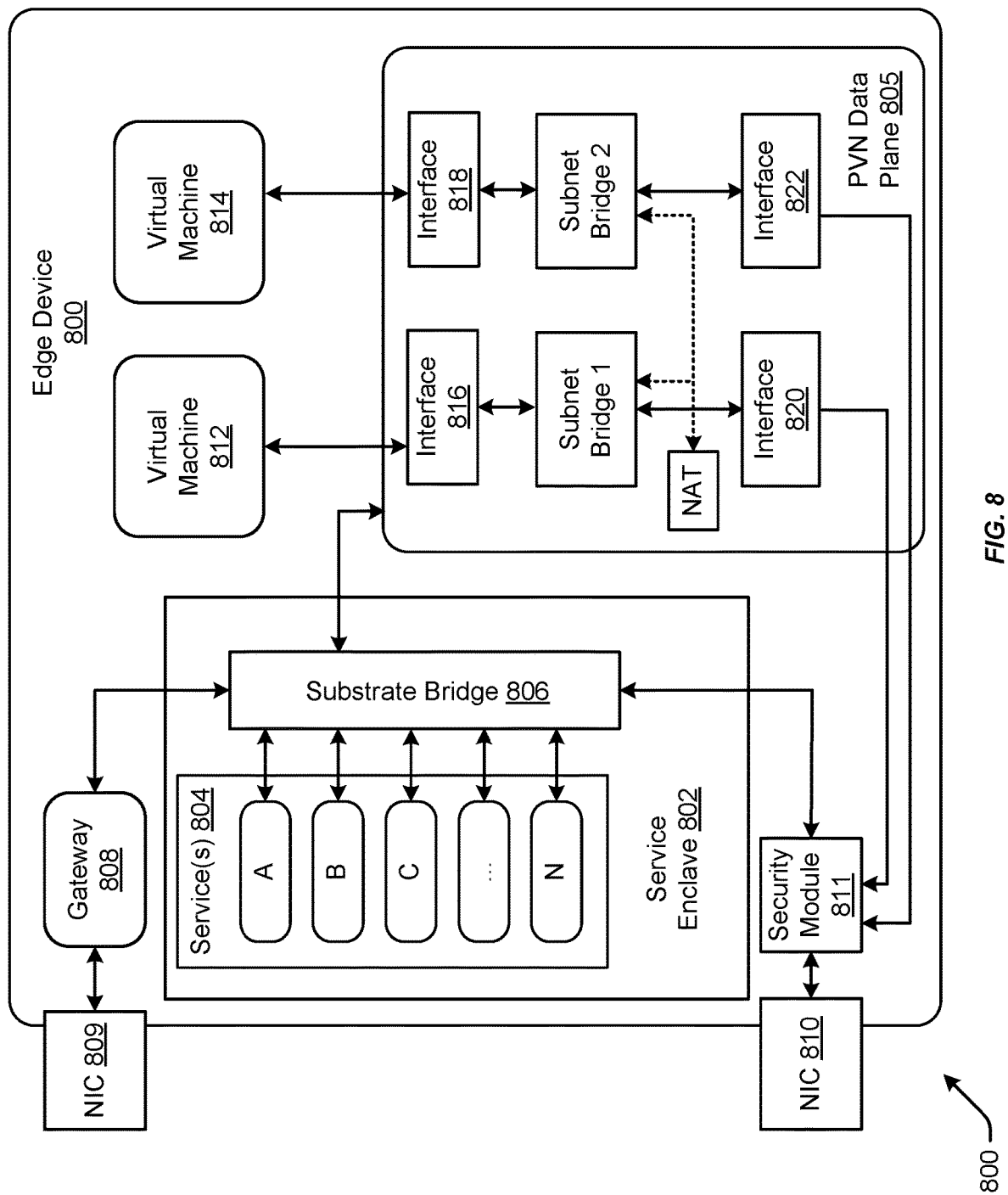
FIG. 8 is a block diagram depicting an edge device that includes a service enclave, according to at least one embodiment.

FIG. 8 is a block diagram depicting an edge device 800 that includes a service enclave 802, according to at least one embodiment. A "service enclave," as used herein, refers to an intra-device and/or inter-device network environment in which network traffic between a set of services (e.g., a predefined set of services) operating at an edge device (or more than one edge device) is isolated. A service enclave, as described herein, may isolate network traffic (e.g., by utilizing different virtual private networks (VPNs) or subnets) between services from other components of the edge device using a virtual substrate network (e.g., a private virtual network that is dedicated to those set of services). In some embodiments, the virtual substrate network may span across multiple edge devices to enable services of one edge device in a computing cluster of edge devices to communicate with services of another edge device of the computing cluster. The edge devices of the computing cluster may be communicatively coupled (e.g., via physical cable(s) and/or wireless technology). Other network traffic of the edge device (e.g., between one or more services and one or more virtual machines or components) may utilize separate networking components (e.g., subnets, virtual private networks, etc.) independent of the service enclave.

FIG. 8 depicts service enclave 802 that may be utilized by service(s) 804 (e.g., an example of the service(s) 502 of FIG. 5). Service(s) 804 may execute on edge device 800 (e.g., an example of the edge devices discussed herein, such as edge device 500 of FIG. 5) and include any suitable combination of a set of predefined services executing at the edge device 800 (e.g., a user interface console service, an authentication control plane service, an authentication data plane service, an application programming interface (API) service (e.g., API service 702 of FIG. 7), a worker service (e.g., worker service 706 of FIG. 7), a virtual cloud network API service, a private virtual network control plane, a private virtual network data plane (e.g., PVN data plane 805), a block storage service, a service for managing data plane resources (e.g., hypervisor service 708 of FIG. 7), a service for managing functions (e.g., a function-as-a-service service), an events service, an object storage service, a service for managing one or more data stores (e.g., DB 704 of FIG. 7), a domain host configuration protocol (DHCP) service, a domain name service (DNS) service, a network time protocol (NTP) service, and the like).

Each of the service(s) 804 may execute as containers (e.g., Docker containers). Each container may be assigned a substrate IP address (e.g., a static IP address utilized within the service enclave 802). In some embodiments, these substrate IP addresses enable the service(s) 804 to communicate with and/or address traffic to one another within a substrate network (e.g., the substrate network 504 of FIG. 5). In some embodiments, communication between the service(s) 804 on a given edge device may be encrypted or unencrypted, while communications between services of different edge devices may be encrypted. By way of example, communications between any of the service(s) 804 and service of another edge device may be encrypted with an encryption protocol (e.g., MACsec). In some embodiments, the encryption protocol may be configured at provisioning time before the edge device is shipped to the customer. A service enclave (e.g., the service enclave 802) may be configured as a secure environment protected with a secure boot framework (e.g., TrenchBoot). A secure boot framework may refer to a framework that allows security engines to be built to perform launch integrity actions for the system. In some embodiments, a secure boot framework may build upon Boot Integrity Technologies (BITs) that establish one or more Roots of Trust (RoT) from which a degree of confidence that integrity actions were not subverted. Customers are excluded from accessing the service enclave(s) and the substrate network(s) disclosed herein. The service enclave(s) and substrate network(s) utilized herein may be dedicated to network traffic between services of one or more edge devices. By way of example, the service enclave 802 may be utilized by service(s) 804 to execute a local and/or distributed control plane operations at the edge device 800 or amongst a cluster of edge devices that includes the edge device 800.

Service(s) 804 may be connected to one another and the substrate network (e.g., the substrate network 504 of FIG. 5) via substrate bridge 806. Substrate bridge 806 may be configured to connect one or more service(s) 804 with containers, virtual machines, and other services executing on edge device 800. The substrate network on each edge device can be bridged together so that all of the services of the edge devices appear on a common subnet. For isolation, this substrate subnet may be used within a virtual private network to ensure that network traffic between services remains separate from customer network traffic (e.g., non-service-based network traffic). Security module 811 may be configured to encrypt traffic between edge devices using a security protocol (e.g., macsec, etc.). In some embodiments, the security module 811 may be a MACsec device (e.g., a Linux MACsec device) implemented in the network stack of an edge device (e.g., edge device 800). In some embodiments, the security module 811 may implement IPsec as the security protocol or encryption protocol. Similar to MACsec, IPsec can provide encryption to network packets transmitted between edge devices on the intra-node network. IPsec may not secure network infrastructure traffic (e.g., DHCP, ARP, neighbor discovery, etc.), but can allow for routing of encrypted packets between different LANs. An IPsec protocol may establish a mesh network between all the edge devices in a distributed computing cluster (e.g., the distributed cluster 600 of FIG. 6 to which edge device 800 participates).

Private virtual network (PVN) data plane 805 may be connected to service(s) 804 via substrate bridge 806. Gateway 808 may operate as part of or separate from the PVN data plane 805. Gateway 808 may be a gateway for a public internet, a public network, a client network, of the like (e.g., network 520 of FIG. 5), distinguishable from the substrate network (e.g., substrate network 504 of FIG. 5) that may process intra-node traffic between edge device 800 and other edge devices within a distributed computing cluster (e.g., a distributed computing cluster in which edge device 800 participates). NIC 810 may be configured to communicatively connect the service(s) 804 to the substrate network (e.g., the substrate network 504 of FIG. 5, the substrate network 606 of FIG. 6, not depicted within FIG. 8). NIC 809 may be connect the edge device 800 to the public internet, public network, client network, or the like (e.g., the network 520 of FIG. 5). In some embodiments, during a cluster installation process in which one or more edge devices are configured as part of a computing cluster, at least one edge device (e.g., edge device 800) of the cluster can be connected (e.g., via NIC 809) to a customer's network (e.g., an on-premise network, at a location associated with the customer, remote to a centralized data center associated with the customer and/or lacking a public/private network connection to such a centralized data center (e.g., via an Internet connection, a VPN connection, a dedicated connection, etc.). The customer may provide a static IP address for that link. Gateway 808 may be configured to include IP table rules that map service ports of the edge device 800 (e.g., ports that are assigned to each service) to that customer-provided external IP address. Request traffic sent to those ports may be translated into the substrate network.

The PVN data plane 805 may represent a virtual smart network interface card (VSNIC) and may be an example of the virtual NIC(s) 506 of FIG. 5. The edge device 800 may be similar to other edge devices described herein, including edge device 204 of FIG. 2 and edge device 500 of FIG. 5. The PVN data plane 805 may be a data plane corresponding to the PVN(s) 505 of FIG. 5. As a data plane, the PVN data plane 805 may include a collection of software (e.g., processes, threads, workloads, applications, modules, and the like) configured to support the data operations (e.g., sending, receiving, negotiating connections, etc.) for the PVN(s). The PVN(s) may include networks for use by one or more virtual machines (e.g., virtual machine (VM) 812, VM 814, each an example of the VM(s) 508 of FIG. 5), one or more containers, one or more services (e.g., service(s) 804, an example of the service(s) 502 of FIG. 5) and/or other processes or services executing on the edge device 800. The PVN(s) may also interface with additional networks, including a client network or public network, network 520 of FIG. 5 and/or a substrate network such as substrate network 504 of FIG. 5). Physical network interfaces (e.g., NIC 809, NIC 810) of the edge device 800 may be examples of other physical NICs described herein (e.g., NIC1-NIC4 of FIG. 5) and may provide one or more physical network connections (e.g., RJ45, QSFP28, etc.) between devices (e.g., one or more edge devices including edge device 800) via one or more networks (e.g., substrate network 504, network 520 of FIG. 5, respectively).

The PVN data plane 805 may execute in one or more containers by the edge device 800. For example, networking services including gateway module (e.g., gateway 808), a domain name system (DNS) service (not depicted), a network time protocol (NTP) service (not depicted), and other smart network interface card (SNIC) service(s) (not depicted) may each execute as its own container. The containers may utilize a separate networking namespace for each container. As used herein, networking namespace refers to an instance (e.g., a logical copy) of the network stack of the host device. The network stack in turn may refer to the configuration of all associated networking functionality of host device for the relevant networking layers (e.g., physical, networking, transport, application, etc.), including port configurations, routing tables, addressing, networking interfaces, virtual networking devices (e.g., bridges, virtual local area networks (VLANs), virtual Ethernet ports, other interfaces, etc.), drivers, protocols, protocol configuration, and the like. Thus, PVN data plane 805 may provide distinct networking namespaces for different portions of the PVN data plane 805. The execution of the PVN data plane 805 components may be supported by the host operating system (e.g., operating system 112 of FIG. 1), containerization engine (e.g., containerization engine 102 of FIG. 1), and/or hypervisor (e.g., hypervisor 106 of FIG. 1).

As depicted in FIG. 8, some of the components of the PVN data plane 805 may be configured to provide network interfaces, subnets, routing tables, firewall, network address translation (NAT), and/or other networking functionality for the PVN data plane 805. The PVN data plane 805 may be associated with an object (e.g., an object associated with a virtual cloud network VCN), an external IP address, a subnet object, a subnet IP address, a bump IP address, a port map object list, a security group, and the like. The PVN data plane 805 may implement any suitable number of virtual private networks and any suitable subnets. A virtual private network may include a collection of interfaces (e.g., interface 816, 818, 820, 822, etc.) that can communicate directly to other interfaces (e.g., some or all of the other interfaces within that virtual private network). Each virtual private network can use any suitable private IP address range (e.g., a particular subnet). The isolation allows any virtual network to use overlapping IP ranges.

In some examples, the PVN data plane 805 can include virtual network interfaces configured to connect one or more virtual machines of the edge device 800 to a PVN. For example, PVN data plane 805 may provide one or more virtual network interfaces (e.g., interfaces 816 and 818). The interface 816 and 818 may individually include endpoints of a virtual networking device. For example, interface 816 can include two virtual network devices (e.g., Linux virtual Ethernet (veth) devices, also referred to as a "virtual network device pair"). A virtual network device pair may be linked such that network traffic (e.g., packets, frames, etc.) sent to one virtual network device (a first veth device) is received at the paired device (a second veth device) similar to data transmitted over a physical Ethernet wire. The endpoints of a given network interface (e.g., two veth devices of interface 816) may form a virtual wire within the PVN data plane 805 from VM 812 to a particular VPN (referred to as "VPN 1"). Similarly, interface 818 may form (e.g., via another pair of veth devices) a virtual wire between VM 814 and the same or another VPN (referred to as "VPN 2"). Interfaces 816 and 818 may form a virtual wire from VMs 812 and 814 to subnet bridges 1 and 2, respectively. Any suitable virtual machine (e.g., VM1 806) may participate in multiple subnets and may be assigned multiple IP addresses corresponding to the subnets in which it participates.

In some embodiments, endpoints of virtual network interfaces may be configured in different networking namespaces. For example, an endpoint of an interface (e.g., one veth device of interface 816) may be in a first networking namespace associated with the PVN data plane 805, while another endpoint (e.g., a second veth device) may be in a second networking namespace associated with the PVN data plane 805. The first networking namespace may be the networking namespace of the host operating system, while the second networking namespace may be a namespace associated with the PVN data plane 805 and/or a module of the PVN data plane 805. An endpoint in one networking namespace may be configured as a device of that namespace, with addresses and routing information corresponding to that namespace. For example, interface 816 may include a virtual network device (e.g., a virtual Ethernet device) in the host operating system namespace, while the other endpoint of interface 816 (e.g., another virtual Ethernet device) may be a virtual network device in another namespace. In this way, a virtual network interface (e.g., interface 816) may provide an interface for virtual machine 812 to a private virtual network provided by the PVN data plane 805.

In some embodiments, PVN data plane 805 may implement one or more subnets in conjunction with one or more PVNs. For example, a first PVN may be associated with a first subnet, while a second PVN may be associated with a second subnet. A PVN may include one or more VNICs (e.g., virtual NIC(s) 506 of FIG. 5); a subnet bridge for the PVN may bridge any suitable number of the VNICs of the PVN. The PVN data plane 805 may include one or more subnet bridges (e.g., subnet bridge 1, subnet bridge 2, etc.) corresponding to the PVNs within the distributed computing cluster.

Although not shown in FIG. 8, PVN data plane 805 may also include a dynamic host control protocol (DHCP) service for subnet bridges 1 and 2. The DHCP service may provide dynamic addressing for devices associated with subnet bridges 1 and 2, including the endpoints of interfaces 816, 818, 820, and 822.

To connect the one or more PVNs to other networks of the distributed computing cluster (e.g., network 520, substrate network 504 of FIG.), the PVN data plane 805 can include additional network interfaces (e.g., interfaces 820 and/or 822). Interfaces 820 and 822 may include corresponding pairs of virtual network devices (e.g., virtual Ethernet devices) within the networking namespace of the PVN data plane 805. For instance, interface 820 may be a virtual network device configured to connect to network 520. Similarly, interface 822 may be a virtual network device (e.g., a virtual Ethernet device) configured to connect to a substrate network (an example of the substrate network 504 of FIG. 5, including service enclave 802).

Figure 9:
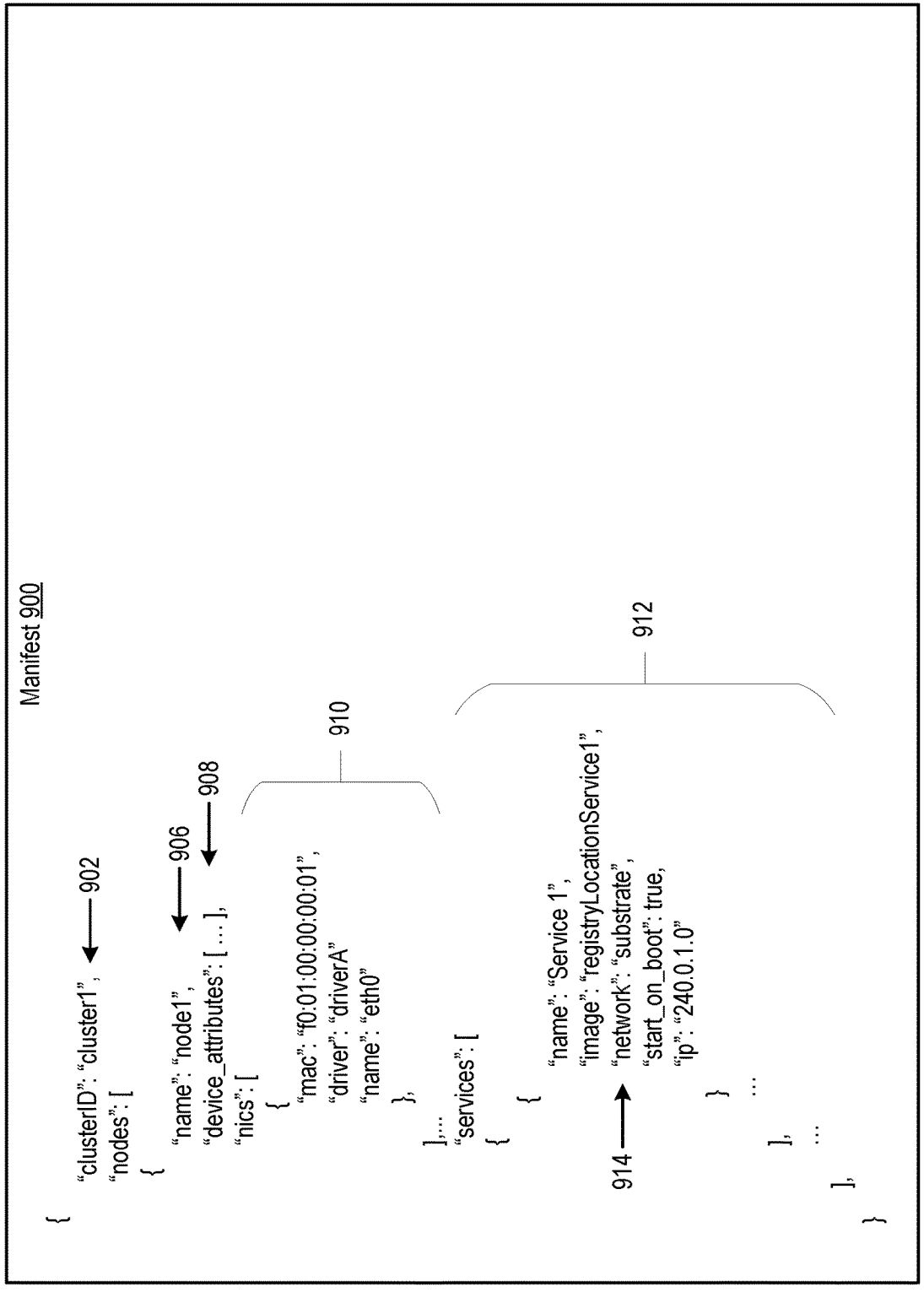
FIG. 9 is a block diagram depicting an example manifest that includes information with which a service enclave can be configured, in accordance with at least one embodiment.

FIG. 9 is a block diagram depicting an example manifest 900 that includes information with which a service enclave can be configured, in accordance with at least one embodiment. Manifest 900 may define the configuration of multiple edge devices to be operated as a cluster. In some embodiments, manifest 900 may define a cluster identifier at 902. Any suitable number of nodes may be provided in section 904. In some embodiments, a node (e.g., edge device 800 of FIG. 1) may be assigned a name as depicted at 906. The manifest 900 may indicate a set of device attributes for a given node (e.g., the edge device 800) at 908.

A manifest may include any suitable information pertaining to one or more network interface cards (e.g., physical and/or virtual network interface cards). A network interface card may be defined within the manifest 900 as having a media access control (MAC) address or another suitable identifier such as a name. In some embodiments the manifest 900 may identify a driver for a network interface card within section 910. Section 910 may include any suitable number of NIC definitions.

A manifest may identify any suitable number of services. Manifest 900 depicts at least one service. Within the manifest, various service level attributes may be identified. By way of example, section 912 may include a name for the service (e.g., "Service 1"), a location at which the image for the service can be found (e.g., "registryLocationService1"), a default network name within which the service will operate (e.g., "substrate"), an indicator indicating whether the service will start on boot (e.g., "true"), and an IP address for the service (e.g., 240.0.1.0). The manifest 900 may specify aspects of any suitable number of services within section 912. For example and as depicted at 914, the manifest 900 may indicate that a service (e.g., Service 1, an example of the service(s) 804 of FIG. 8) may participate in a substrate network (e.g., the substrate network 504 of FIG. 5). In some embodiments, the manifest 900 may specify an IP address (e.g., 240.0.1.0) within the substrate network for the service (e.g., "Service 1"). In some embodiments, a manifest may indicate one or more networks in which a given service may participate. The manifest may further specify any suitable number of IP addresses for a given service within these networks.

Although the manifest 900 is depicted as including a certain attributes of a cluster, a node, or a device, it should be appreciated that a manifest may identify any suitable attribute of a cluster, node, or a device. Thus, the example attributes depicted in FIG. 9 are not intended to be considered an exhaustive list of the possible attributes that may be included in any given manifest.

Figure 10:
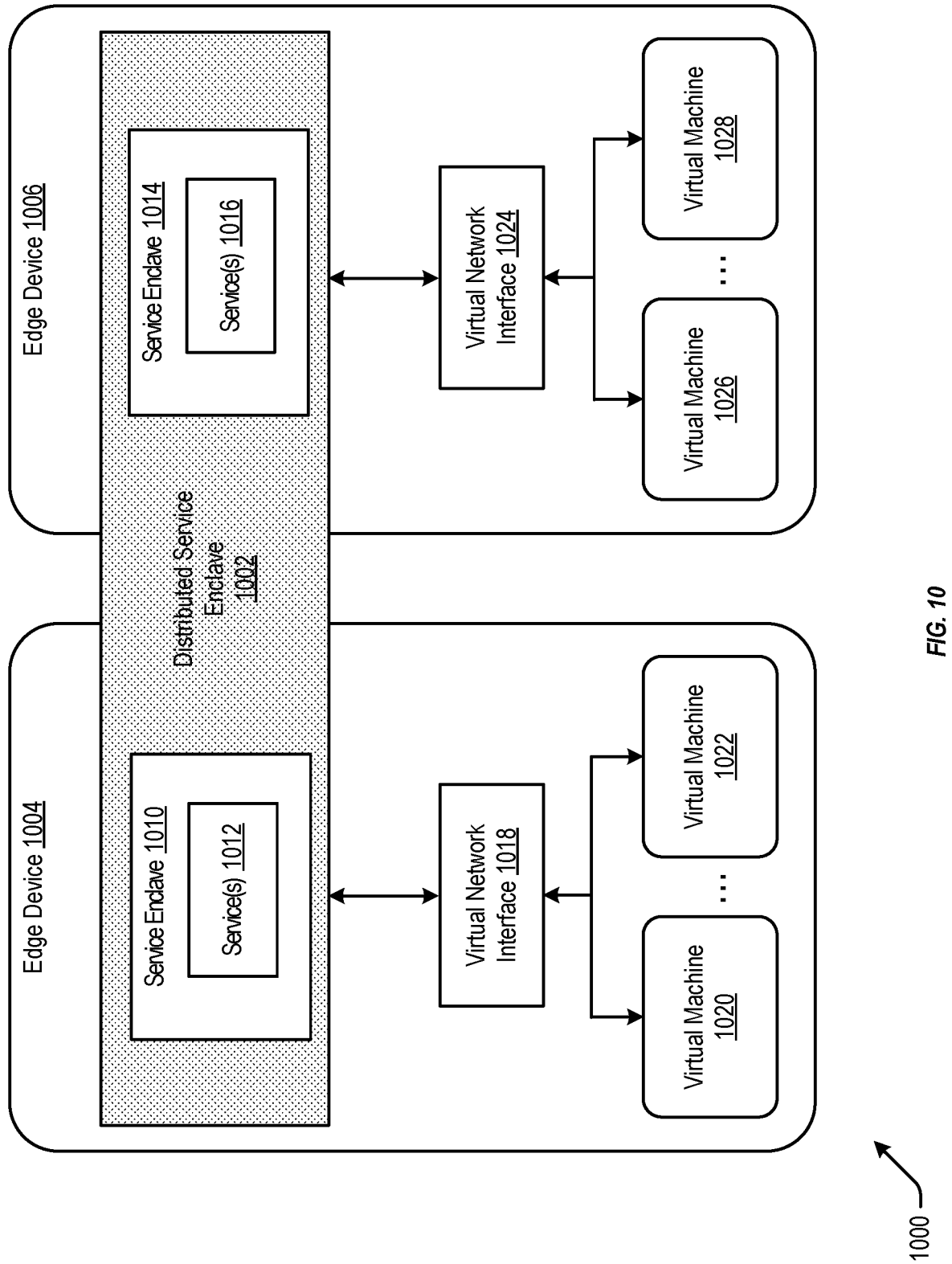
FIG. 10 is a block diagram of an example distributed computing cluster that includes a distributed service enclave, according to at least one embodiment.

FIG. 10 is a block diagram of an example of a distributed computing cluster 1000 that includes a distributed service enclave 1002, according to at least one embodiment. The distribute service enclave 1002 may span any suitable number of edge devices. As depicted, the distributed service enclave 1002 spans across edge device 1004 and edge device 1006, both of which are examples of the edge devices described in the aforementioned figures. Edge devices 1004 and 1006 may participate in a distributed computing cluster (e.g., the distributed computing cluster 600 of FIG. 6). Edge device 1004 (an example of the edge device 800 of FIG. 8) may include service enclave 1010 in which service(s) 1012 (an example of service(s) 804 of FIG. 8) participate. Similarly, edge device 1006 may include service enclave 1014 in which service(s) 1016 participate. As used herein, distributed service enclave 1002 may also be referred to as a "service enclave." Distributed service enclave 1002, service enclave 1010, and/or service enclave 1014) are each intended to be an example of a service enclave as utilized herein. Although only two edge devices are depicted in FIG. 10, any suitable number of edge devices may be likewise utilized. The edge devices 1004 and 1006 may be communicatively connected via one or more switches (e.g., switches 608 and/or 610 of FIG. 6).

The edge devices 1004 and 1006 may, individually and/or collectively, provide infrastructure and corresponding sets of services that enable customers to build and run a wide range of applications (e.g., compute instances), services, and/or storage in a highly available, physically local, and virtual hosted environment. The specific configuration of the edge devices 1004 and 1006 with respect to the distributed service enclave 1002, service enclaves 1010 and 1014, service(s) 1012 and 1016, and/or any suitable combination of virtual network interfaces 1018 and 1024, and virtual machines 1020, 1022, 1026, and 1028 may be specified within a manifest (e.g., manifest 900 of FIG. 9). In some embodiments, a customer (e.g., a user of the computing cluster in which edge devices 1004 and 1006 participate) does not manage or control the underlying physical resources provided by the edge devices of FIG. 10 and the aforementioned figures, but has control over expanding or reducing virtual machines (e.g., compute instances (e.g., virtual machines 1020, 1022, 1026, 1028), virtual interfaces (e.g., virtual network interfaces 1018, 1024 (each an example of a virtual NIC)), block or object storage, and the like), deploying applications to those virtual machines, and the like.

An intra-node switch (e.g., switch 608 and/or 610 of FIG. 6) can provide network switching functionality in accordance with one or more networking standards (e.g., Ethernet). In particular, the intra-node switch can provide packet switching for all packets transmitted between edge devices in the cluster including between edge devices 1004 and 1006. The topology of the distributed computing cluster in which edge devices 1004 and 1006 participate may be specified within manifest 900 as described above. In some embodiments, only one edge device (e.g., edge device 1004) may connect (e.g., via a same or different switch) to a client device (e.g., user device 202 of FIG. 2). Data received from the client device (e.g., at edge device 1004) may be propagated to the other edge devices (e.g., to edge device 1006) via the intra-node network (e.g., a substrate network 504 of FIG. 5, implemented as the distributed service enclave 1002 of FIG. 10).

As a non-limiting example, the edge devices 1004 and 1006 may individually provide a wide variety of infrastructure components (e.g., services, virtual machines (VMs), containers, etc.) to support cloud computing within the distributed computing cluster (e.g., the distributed computing cluster 600). In some embodiments, the edge computing devices (e.g., edge devices 1004 and 1006) may implement a distributed control plane configured to perform operations related to managing the infrastructure services and components. For example, a control plane (CP) of a given edge device (e.g., edge device 1004) may send instructions (e.g., to hypervisor service 708 of FIG. 7 operating at edge device 1004) to provision one or more VMs configured to execute tasks. A distributed CP may be distributed over two or more edge devices (e.g., any suitable combination including at least two of edge devices 1004 and 1006) in the distributed computing cluster, such that the CP services hosted on individual edge devices provide the distributed CP. In this way, the distributed CP may access hardware and software resources of any edge device in the cluster to perform CP operations. For example, a CP service of the distributed CP (e.g., a CP service executing on edge device 1004) may perform operations to instruct a hypervisor of edge device 1006 to provision a VM on edge device 1006.

Data transmission between the edge devices (e.g., distributed CP traffic, application traffic, etc.) may be transmitted within the distributed service enclave 1002 (e.g., via a substrate network of the distributed service enclave 1002). To secure the network traffic between edge devices of the distributed computing cluster 1000, each edge device may provide a security module (e.g., security modules 811 of FIG. 8, or the like) configured to encrypt transmitted data according to an encryption protocol or other security protocol. In some embodiments, the security module (e.g., the security module 811) may be implemented in software.

In some embodiments, the configuration of nodes (e.g., edge devices 1004 and 1006) in the distributed computing cluster may be static, such that the number of edge devices is fixed at the time of provisioning the distributed computing cluster 1000 (e.g., at a client site). The configuration of the distributed computing cluster 1000 may be specified by manifest 900 of FIG. 900. In some embodiments, failed edge devices may be replaced with another edge device configured with identical parameters as the failed device.

Figure 11:
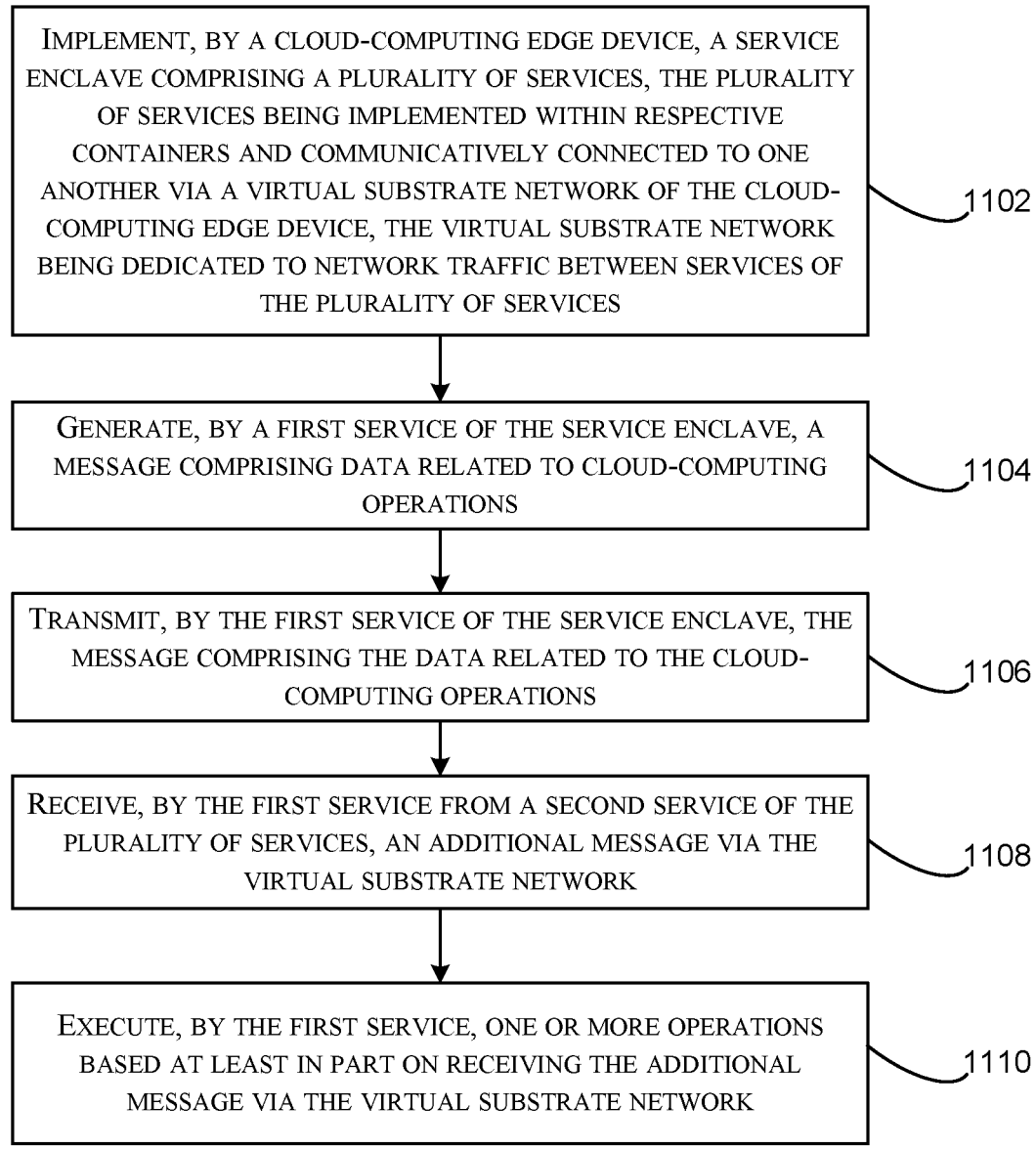
FIG. 11 illustrates an example method for utilizing a service enclave of an edge device, according to at least one embodiment.

FIG. 11 illustrates an example method 1100 for utilizing a service enclave (e.g., the service enclave 802 of FIG. 8, the distributed service enclave 1002 of FIG. 10) of an edge device (e.g., edge device 800 of FIG. 8, edge device 1004 of FIG. 10, etc.), according to at least one embodiment. The operations of FIG. 11 may be performed in conjunction with one or more of the operations performed by any suitable edge device (e.g., the edge device 800). In some embodiments, the edge device may participate in a distributed computing cluster (e.g., the distributed computing cluster 1000 of FIG. 10) including a plurality of cloud-computing edge devices (e.g., edge devices 1004 and 1006) described above with respect to FIG. 10. The operations described in method 1100 may be performed in any suitable order. Although a number of operations are described with respect to FIG. 11, more or fewer operations may be performed.

The method 1100 may begin at 1102, where a service enclave (e.g., service enclave 802 of FIG. 8, service enclave 1010 of FIG. 10, etc.) comprising a plurality of services (e.g., service(s) 804 of FIG. 8, service(s) 1012 of FIG. 10). In some embodiments, the plurality of services may be implemented within respective containers (e.g., Docker containers, or the like) and communicatively connected to one another via a virtual substrate network (e.g., the service enclave 802 of FIG. 8) of the cloud-computing edge device. In some embodiments, the virtual substrate network may be dedicated to network traffic between services of the plurality of services.

At 1104, a message comprising data related to cloud-computing operations may be generated by a first service of the service enclave (e.g., the service labeled "A" in FIG. 8).

At 1106, the message comprising the data related to the cloud-computing operations may be transmitted by the first service of the service enclave. By way of example, service "A" may transmit a message to service "B" of the service enclave 802 of FIG. 8. In some embodiments, the first service can transmit the message to another service operating at a different edge device (e.g., when the edge device participates in a distributed computing cluster such as distributed computing cluster 1000 of FIG. 10) via the service enclave.

At 1108, an additional message may be received by the first service from a second service of the plurality of services via the virtual substrate network. By way of example, service "A" may receive the additional message from service "B" of service(s) 804 of FIG. 8 (and/or from any of the services of service(s) 804).

At 1110, one or more operations may be executed by the first service (e.g., service "A") based at least in part on receiving the additional message via the virtual substrate network.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method, comprising:
   implementing, by a plurality of cloud-computing edge devices, a plurality of distributed computing clusters that operate as respective isolated computing clusters that individually lack a network connection to a cloud-provider network, each of the plurality of distributed computing clusters implementing a respective distributed service enclave comprising a plurality of services that are implemented within respective containers and communicatively connected to one another, according to a manifest, by an intra-node switch and by a distributed virtual substrate network, the distributed virtual substrate network being dedicated to network traffic of the plurality of services and distributed across a set of cloud-computing edge devices corresponding to the respective distribute service enclave, each respective distribute service enclave implementing a respective distributed control plane that manages infrastructure components and services of a respective distributed computing cluster, a network topology of each respective distributed service enclave being predefined by the manifest;
   generating, by a first service of the respective distributed service enclave, a message comprising data related to cloud-computing operations;
   transmitting, by the first service of the respective distributed service enclave, the message comprising the data related to cloud-computing operations;
   receiving, by the first service from a second service of the plurality of services, an additional message via the distributed virtual substrate network; and
   executing, by the first service, one or more operations based at least in part on receiving the additional message via the distributed virtual substrate network.

2. The computer-implemented method of claim 1, wherein the network traffic between the plurality of services of the respective distributed service enclave is unencrypted, and wherein external network traffic between a plurality of distributed service enclaves is encrypted.

3. The computer-implemented method of claim 1, wherein the plurality of services comprise a gateway service that enables communication between a client device and the plurality of services.

4. The computer-implemented method of claim 1, further comprising encrypting the message prior to transmitting the message from a first cloud-computing edge device of the plurality of cloud-computing edge devices to a second cloud-computing edge device of the plurality of cloud-computing edge devices.

5. The computer-implemented method of claim 1, wherein each of the plurality of cloud-computing edge devices comprise a security module that is configured to encrypt traffic between the plurality of cloud-computing edge devices.

6. The computer-implemented method of claim 1, wherein a first cloud-computing edge device of the respective distributed control plane performs operations related to managing the infrastructure components and services of a second cloud-computing edge device of the plurality of cloud-computing edge devices.

7. The computer-implemented method of claim 1, wherein a single cloud-computing edge device of an isolated computing cluster is configured to connect with a client device, and wherein the single cloud-computing edge device is further configured to propagate data received from the client device to at least one additional cloud-computing edge device of the isolated computing cluster.

8. A computing cluster, comprising:
an intra-node switch;
a plurality of cloud-computing edge devices communicatively connected to one another via the intra-node switch, the plurality of cloud-computing edge devices individually comprising one or more processors and one or more memories storing computer-executable instructions that, when executed with the one or more processors, cause a cloud-computing edge device to:
implement, by a plurality of distributed computing clusters comprising the computing cluster that operate as respective isolated computing clusters that individually lack a network connection to a cloud-provider network, each of the plurality of distributed computing clusters implementing a respective distributed service enclave comprising a plurality of services that are implemented within respective containers and communicatively connected to one another, according to a manifest, by the intra-node switch and by a distributed virtual substrate network, the distributed virtual substrate network being dedicated to network traffic of the plurality of services and distributed across a set of cloud computing services corresponding to the respective distributed service enclave, each respective distribute service enclave implementing a respective distributed control plane that manages infrastructure components and services of a respective distributed computing cluster, a network topology of each respective distributed service enclave being predefined by the manifest;
generate, by a first service of the respective distributed service enclave, a message comprising data related to cloud-computing operations;
transmit, by the first service of the respective distributed service enclave, the message comprising the data related to cloud-computing operations;
receive, by the first service from a second service of the plurality of services, an additional message via the distributed virtual substrate network; and
execute, by the first service, one or more operations based at least in part on receiving the additional message via the distributed virtual substrate network.

9. The computing cluster of claim 8, wherein the network traffic between the plurality of services of the respective distributed service enclave is unencrypted, and wherein external network traffic between a plurality of distributed service enclaves is encrypted.

10. The computing cluster of claim 8, wherein the plurality of services comprise a gateway service that enables communication between a client device and the plurality of services.

11. The computing cluster of claim 8, wherein executing the computer-executable instructions further causes the one or more processors to encrypt the message prior to transmitting the message from a first cloud-computing edge device of the plurality of cloud-computing edge devices to a second cloud-computing edge device of the plurality of cloud-computing edge devices.

12. The computing cluster of claim 8, wherein each of the plurality of cloud-computing edge devices comprise a security module that is configured to encrypt traffic between the plurality of cloud-computing edge devices.

13. The computing cluster of claim 8, wherein a first cloud-computing edge device of the respective distributed control plane performs operations related to managing the infrastructure components and services of a second cloud-computing edge device of the plurality of cloud-computing edge devices.

14. The computing cluster of claim 8, wherein a single cloud-computing edge device of an isolated computing cluster is configured to connect with a client device, and wherein the single cloud-computing edge device is further configured to propagate data received from the client device to at least one additional cloud-computing edge device of the isolated computing cluster.

15. A non-transitory computer-readable storage medium comprising computer-executable instructions that, when executed by one or more processors of a cloud-computing edge device, causes the cloud-computing edge device to:
implement, by the plurality of distributed computing clusters that operate as respective isolated computing clusters that individually lack a network connection to a cloud-provider network, each of the plurality of distributed computing clusters implementing a respective distributed service enclave comprising a plurality of services that are implemented within respective containers and communicatively connected to one another, according to a manifest, by an intra-node switch and by a distributed virtual substrate network, the distributed virtual substrate network being dedicated to network traffic of the plurality of services and distributed across a set of cloud computing services corresponding to the respective distributed service enclave, each respective distribute service enclave implementing a respective distributed control plane that manages infrastructure components and services of a respective distributed computing cluster, a network topology of each respective distributed service enclave being predefined by the manifest;

generate, by a first service of the respective distributed service enclave, a message comprising data related to cloud-computing operations;

transmit, by the first service of the respective distributed service enclave, the message comprising the data related to cloud-computing operations;

receive, by the first service from a second service of the plurality of services, an additional message via the distributed virtual substrate network; and execute, by the first service, one or more operations based at least in part on receiving the additional message via the distributed virtual substrate network.

16. The non-transitory computer-readable storage medium of claim 15, wherein the network traffic between the plurality of services of the respective distributed service enclave is unencrypted, and wherein external network traffic between a plurality of distributed service enclaves is encrypted.

17. The non-transitory computer-readable storage medium of claim 15, wherein executing the computer-executable instructions further causes the one or more processors to encrypt the message prior to transmitting the message from a first cloud-computing edge device of a plurality of cloud-computing edge devices to a second cloud-computing edge device of the plurality of cloud-computing edge devices.

18. The non-transitory computer-readable storage medium of claim 15, wherein each of the cloud-computing edge device comprises a security module that is configured to encrypt traffic between the cloud-computing edge device and a plurality of cloud-computing edge devices.

19. The non-transitory computer-readable storage medium of claim 15, wherein a first cloud-computing edge device of the respective distributed control plane performs operations related to managing the infrastructure components and services of a second cloud-computing edge device of a plurality of cloud-computing edge devices.

20. The non-transitory computer-readable storage medium of claim 15, wherein a single cloud-computing edge device of an isolated computing cluster is configured to connect with a client device, and wherein the single cloud-computing edge device is further configured to propagate data received from the client device to at least one additional cloud-computing edge device of the isolated computing cluster.

* * * * *